US011213613B2

(12) United States Patent
Dai et al.

(10) Patent No.: US 11,213,613 B2
(45) Date of Patent: Jan. 4, 2022

(54) THREE-DIMENSIONAL TISSUE SCAFFOLD WITH STEM CELL ATTRACTING ELEMENT AND USE THEREOF

(71) Applicant: INSTITUTE OF GENETICS AND DEVELOPMENTAL BIOLOGY, CHINESE ACADEMY OF SCIENCES, Beijing (CN)

(72) Inventors: Jianwu Dai, Beijing (CN); Jie Sun, Suzhou (CN); Bing Chen, Beijing (CN); Zhifeng Xiao, Beijing (CN)

(73) Assignee: INSTITUTE OF GENETICS AND DEVELOPMENTAL BIOLOGY, CHINESE ACADEMY OF SCIENCES, Beijing (CN)

( * ) Notice: Subject to any disclaimer, the term of this patent is extended or adjusted under 35 U.S.C. 154(b) by 583 days.

(21) Appl. No.: 15/580,678

(22) PCT Filed: Sep. 30, 2015

(86) PCT No.: PCT/CN2015/091190
§ 371 (c)(1),
(2) Date: Dec. 7, 2017

(87) PCT Pub. No.: WO2016/197491
PCT Pub. Date: Dec. 15, 2016

(65) Prior Publication Data
US 2018/0214612 A1 Aug. 2, 2018

(30) Foreign Application Priority Data
Jun. 12, 2015 (WO) ................ PCT/CN2015/081375

(51) Int. Cl.
*A61L 27/54* (2006.01)
*A61L 27/24* (2006.01)
*A61L 27/56* (2006.01)
*C07K 16/18* (2006.01)
*A61L 27/22* (2006.01)
*A61K 38/08* (2019.01)
*A61K 38/19* (2006.01)
*A61K 47/42* (2017.01)
*A61L 27/58* (2006.01)
*C07K 7/06* (2006.01)
*C07K 14/52* (2006.01)
*A61K 38/00* (2006.01)

(52) U.S. Cl.
CPC .............. *A61L 27/54* (2013.01); *A61K 38/08* (2013.01); *A61K 38/195* (2013.01); *A61K 47/42* (2013.01); *A61L 27/227* (2013.01); *A61L 27/24* (2013.01); *A61L 27/56* (2013.01); *A61L 27/58* (2013.01); *C07K 7/06* (2013.01); *C07K 14/522* (2013.01); *A61L 2300/25* (2013.01); *A61L 2300/252* (2013.01); *A61L 2300/414* (2013.01); *A61L 2300/602* (2013.01); *A61L 2430/20* (2013.01); *A61L 2430/30* (2013.01); *A61L 2430/38* (2013.01); *C07K 2319/70* (2013.01)

(58) Field of Classification Search
CPC .... C07K 16/24; C07K 2319/33; C07K 14/78; C07K 16/18; C07K 2319/32
See application file for complete search history.

(56) References Cited

U.S. PATENT DOCUMENTS

| RE30,985 E | 6/1982 | Cartaya | |
|---|---|---|---|
| 4,560,655 A | 12/1985 | Baker | |
| 4,657,866 A | 4/1987 | Kumar | |
| 4,767,704 A | 8/1988 | Cleveland et al. | |
| 4,927,762 A | 5/1990 | Darfler | |
| 5,122,469 A | 6/1992 | Mather et al. | |
| 2002/0019516 A1* | 2/2002 | Noff | C08H 1/06 530/356 |
| 2002/0156014 A1* | 10/2002 | Lal | C07K 14/47 435/252.3 |
| 2003/0131386 A1* | 7/2003 | Samaha | C07K 14/415 800/289 |
| 2004/0147016 A1* | 7/2004 | Rowley | A61L 27/54 435/325 |
| 2005/0020528 A1* | 1/2005 | Herrmann | A61K 39/3955 514/44 R |
| 2008/0097280 A1* | 4/2008 | Martin | A61K 41/00 604/21 |
| 2009/0305352 A1* | 12/2009 | Dai | A61L 27/227 435/69.7 |
| 2010/0129341 A1 | 5/2010 | Sakon et al. | |

(Continued)

FOREIGN PATENT DOCUMENTS

| CN | 104001212 A | 8/2014 |
|---|---|---|
| CN | 106237384 A | 12/2016 |

(Continued)

OTHER PUBLICATIONS

Ku et al. (2006) Collagen synthesis by mesenchymal stem cells and aortic valve interstitial cells in response to mechanical stretch, Cardiovascul. Res., vol. 71, pp. 548-556.*

(Continued)

*Primary Examiner* — Scarlett Y Goon
*Assistant Examiner* — Samuel W Liu
(74) *Attorney, Agent, or Firm* — Jun He Law Offices P.C.; Zhaohui Wang

(57) ABSTRACT

Provided is a three dimensional tissue scaffold comprising a stem cell attracting element associated with a matrix, and fusion protein of stem cell attracting factor and collagen-binding domain, and methods of uses thereof.

9 Claims, 9 Drawing Sheets
Specification includes a Sequence Listing.

(56) References Cited

U.S. PATENT DOCUMENTS

| | | | | |
|---|---|---|---|---|
| 2010/0166717 A1* | 7/2010 | Penn | ............... | A61K 38/195 424/93.7 |
| 2011/0236355 A1* | 9/2011 | Freed | ............... | C12N 5/0606 424/93.7 |
| 2012/0220729 A1* | 8/2012 | Laemmerhofer | .... | B01D 15/363 525/279 |
| 2013/0108580 A1* | 5/2013 | Leder | ............... | A61K 38/195 424/85.1 |
| 2013/0337017 A1 | 12/2013 | Gensure et al. | | |
| 2013/0345118 A1* | 12/2013 | Rolle | ............... | C07K 14/78 514/2.3 |
| 2014/0370034 A1* | 12/2014 | Purschke | ............... | A61K 47/60 424/178.1 |
| 2015/0335400 A1* | 11/2015 | Mao | ............... | A61C 8/0036 433/175 |

FOREIGN PATENT DOCUMENTS

| | | |
|---|---|---|
| CN | 106279429 A | 1/2017 |
| WO | 87/00195 A1 | 1/1987 |
| WO | 90/03430 A1 | 4/1990 |
| WO | 2010/048418 A1 | 4/2010 |

OTHER PUBLICATIONS

Schesny et al. (2014) Preserved bioactivity and tunable release of a SDF1-GPVI bi-specific protein using photo-crosslinked PEGda hydrogels, Biomaterials, vol. 35, pp. 7180-7187.*

Han, S. et al., "The linear-ordered collagen scaffold-BDNF complex significantly promotes functional recovery after completely transected spinal cord injury in canine", Biomaterials (Feb. 2015), vol. 41, pp. 89-96.

Ziegler, M. et al., "The Bispecific SDF1-GPVI Fusion Protein Preserves Myocardial Function After Transient Ischemia in Mice", Circulation (Feb. 2012), vol. 125, pp. 685-696.

Ziegler, M. et al.,"The Bispecific SDF1-GPVI Fusion Protein Preserves Myocardial Function After Transient Ischemia in Mice", Circulation (Feb. 7, 2012), vol. 125, p. 685-696.

Qianqian Han et al., "Linear ordered collagen scaffolds loaded with collagen-binding brain-derived neurotrophic factor improve the recovery of spinal cord injury in rats". Tissue engineenng:Part A, 2009,15(10):2927-2935.

Kyong Su Rho et al., "Electrospinning of collagen nanofibers:effects on the behavior of normal human keratinocytes and early-stage wound healing.", Biomaterials,2006,27(8):1452-1461.

Vincent F.M.Segers et al., "Local delivery of protease-resistant stromal cell derived factor-1 for stem cell recruitment after myocardial infarction", Circulation. 2007; 116(15):1683-1692.

Dongsheng Zhang et al., "Genetically manipulated progenitor cell sheet with diprotin A improves myocardial function and repair of infarcted hearts", Am J Physiol Heart Circ Physiol. Nov. 2010;299(5):H1339-1347.

Chongyang Shen et al., "Conditioned medium from umbilical cord mesenchymal stem cells induces migration and angiogenesis", Mol Med Rep. 2015;12(1):20-30.

Fikru Belema-Bedada et al., "Efficient homing of multipotent adult mesenchymal stem cells depends on FROUNT-mediated clustering of CCR2", Cell Stem Cell. 2008; 2(6):566-575.

P Bhoopathi et al., "MMP-2 mediates mesenchymal stem cell tropism towards medulloblastoma tumors", Gene Ther. 2011;18(7):692-701.

Sang-Mo Kwon, et al., "Specific Jagged-1 signal from bone marrow microenvironment is required for endothelial progenitor cell development for neovascularization", Circulation. 2008; 118(2):157-165.

Yuxin Li, et al., "Notch1 in bone marrow-derived cells mediates cardiac repair after myocardial infarction", Circulation. 2011; 123(8):866-876.

Junming Tang et al., "Vascular endothelial growth factor promotes cardiac stem cell migralion via the PI3K/Akt pathway", Exp Cell Res. 2009;315(20):3521-31.

Z. Q. Gao et al., "The Effect of Epidermal Growth Factor on Chemotaxis of Bone Marrow Mesenchymal Stem Cells in Vitro", Progress of Anatomical Sciences. 2008; 03.

Jurvansuu J. et al., "Transmembrane protein 18 enhances the tropism of neural stem cells for glioma cells", Cancer Res. Jun. 15, 2008;68(12):4614-4622.

Ziu M. et al., "Glioma-produced extracellular matrix influences brain tumor tropism of human neural stem cels", J Neurooncol. Sep. 2006;79(2):125-133.

Liu Y. et al., "Tropism of Bone Marrow Mesenchymal Stem Cells in Neuroblast Differentiation for Stem Cell Factor", Suzhou University Journal of Medical Science. 2010; 04.

Mishima Y. et al., "Chemotaxis of human articular chondrocytes and mesenchymal stem cells", J Orthop Res. 2008;26(10):1407-1412.

Di Lullo, G. A., et al. "Mapping the ligand-binding sites and disease-associated mutations on the most abundant potein in the human, type I collagen". J Biol Chem. 2002; 277(6): 4223-4231.

Matsushita O. et al., "Gene duplication and multiplicity of collagenases in Clostridium histolyticum", J. Bacteria. 1999; 181:923-933.

Deivanayagam C. C. et al.. Novel fold and assembly of the repetitive B region of the Staphylococcus aureus collagen-binding surface protein, Structure, 2000; 8(1):67-78.

Altschul S. F. et al., "Gapped BLAST and PSI-BLAST: a new generation of protein database search programs", Nucleic Acids Res. 1997; 25:3389-3402.

Teicher B. A. and Fricher S. P., "CXCL12 (SDF-1)/CXCR4 pathway in cancer", Clin. Cancer Res. 2010; 16(11):2927-31.

Princen K. et al., "Evaluation of SDF-1/CXCR4-induced Ca2+ signaling by fluorometric imaging plate reader (FLIPR) and flow cytometry", Cytometry A. 2003; 51(1):35-45.

Munson PJ and Rodbard D. Ligand: "a versatile computerized approach for characterization of ligand-binding systems", Anal Biochem. 1980; 107(1): 220-39.

Graham F. L. et al., "Characteristics of a human cell line transformed by DNA from human adenovirus type 5", J. Gen Virol. 1977; 36(1):59-74.

Urlaub G. et al., "Isolation of Chinese hamster cell mutants deficient in dihydrofolate reductase activity", Proc. Natl. Acad. Sci. USA, 1980; 77:4216-4220.

Mather J. P., "Establishment and characterization of two distinct mouse testicular epithelial cell lines", Biol. Reprod. 1980; 23:243-252.

Mather J. P. et al., "Culture of testicular cells in hormone-supplemented serum-free medium", Annals N.Y. Acad. Sci. 1982; 383:44-68.

Barnes D. et al., "Methods for growth of cultured cells in serum-free medium", Anal. Biochem. 1980; 102:255-270.

Garg, T. et al., Scaffold: "a novel earner for cell and drug delivery", Critical reviews in therapeutic drug carrier systems, 2012; 29 (1): 1-63.

De Souza SJ and Brentani R., "Collagen Binding Site in Collagenase Can Be Determined Using the concept of sense-antisense peptide interactions", J Biol Chem. 1992; 267:13763-13767.

Wang Y et al., "Effects of hypoxia on osteogenic differentiation of rat bone marrow mesenchymal stem cells", Molecular and cellular biochemistry. 2012; 362:25-33.

Han, Qianqian et al. "Functional Collagen Bilmaterials and Tissue Regeneration" China Medical Device Information, Vol./, No. 31, 2012 (Dec. 31, 2012), pp. 1-6.

Lin, Hang et al. "The effect of collagen-targeting platelet-derived growth factore on cellularization and vascularization of collagen scaffolds" China Medical Device Information, vol. 27, No./, Aug. 9, 2006 (Aug. 9, 2006), pp. 5708-5714.

Thevenot, P.T. et al., "The effect of incorporation of SDF-1a into PLGA scaffolds on stem cell recruitment and the inflammatory response" Biomaterials, vol. 31, No./, Feb. 24, 2010 (Feb. 24, 2010), pp. 3997-4008.

(56) References Cited

OTHER PUBLICATIONS

Li, Xiaoran et al., "Electrospum Collagen Fibers with Spatial Patterning of SDF 1a for the Guidance of Neural Stem Cells" Adv. Healthcare Mater., vol. 4, No./, Jun. 29, 2015 (Jun. 29, 2015), pp. 1869-1876.
International Search Report for PCT/CN2015/091190.

* cited by examiner

| SEQ ID NO | Sequences |
|---|---|
| 1 | TKKTLRT |
| 2 | GSAGSAAGSGG |
| 3 | KPVSLSYRCPCRFFESHVARANVKHLKILNTPNCALQIVARLKNNNRQVCIDPKLKWIQEYLEKALNK |
| 4 | MGSSHHHHHHSSGLVPRGSHMKPVSLSYRCPCRFFESHVARANVKHLKILNTPNCALQIVARLKNNNRQVCIDPKLKWIQEYLEKALNKGSAGSAAGSGGTKKTLRT |
| 5 | ACTAAGAAACCCTGCGTACT |
| 6 | GGTAGCGCGGGCAGTGCTGCGGGTTCTGGCGGT |
| 7 | AAGCCCGTCAGCCTGAGCTACAGATGCCCATGCCGATTCTTCGAAAGCCATGTTGCCAGAGCCAACGTCAAGCATCTCAAAATTCTCAACACTCCAAACTGTGCCCTTCAGATTGTAGCCCGGCTGAAGAACAACAACAGACAAGTGTGCATTGACCCGAAGCTAAAGTGGATTCAGGAGTACCTGGAGAAAGCTTTAAACAAG |
| 8 | ATGGGCAGCAGCCATCATCATCATCATCACAGCAGCGGCCTGGTGCCGCGCGGCAGCCATATGAAGCCCGTCAGCCTGAGCTACAGATGCCCATGCCGATTCTTCGAAAGCCATGTTGCCAGAGCCAACGTCAAGCATCTCAAAATTCTCAACACTCCAAACTGTGCCCTTCAGATTGTAGCCCGGCTGAAGAACAACAACAGACAAGTGTGCATTGACCCGAAGCTAAAGTGGATTCAGGAGTACCTGGAGAAAGCTTTAAACAAGGGTAGCGCGGGCAGTGCTGCGGGTTCTGGCGGTACTAAGAAACCCTGCGTACTTGA |

Figure 10

THREE-DIMENSIONAL TISSUE SCAFFOLD WITH STEM CELL ATTRACTING ELEMENT AND USE THEREOF

BACKGROUND OF THE INVENTION

Myocardial infarction (MI), a major cause of mortality throughout the world, leads to the loss of cardiomyocytes, scar formation, and ventricular remodeling. Blood flow restoration to ischemic myocardium is typically done by way of angioplasty or bypass surgery, but these surgeries can only postpone disease progression and they do not induce myocardial regeneration.

Stem cell-based therapy may generate myocardial repair. However, direct transplantation of stem cells into injured hearts has failed to improve cardiac function. Therefore, there exist great needs to effectively recruit endogenous stem cells to injured sites for tissue repair and regeneration.

BRIEF SUMMARY OF THE INVENTION

The present disclosure provides herein three-dimensional tissue scaffolds comprising a stem cell attracting element releasably bound to a matrix.

In certain embodiments, the stem cell attracting element comprises a stem cell attracting factor linked to a binding moiety capable of releasably binding to the matrix.

In certain embodiments, the binding moiety is collagen binding domain (CBD), and the matrix comprises collagen.

In certain embodiments, the stem cell attracting element is a fusion protein comprising stem cell attracting factor linked to the collagen binding domain (CBD).

In certain embodiments, the CBD is derived from a collagenase.

In certain embodiments, the CBD has a length of no more than 20 amino acid residues.

In certain embodiments, the CBD has an amino acid sequence of SEQ ID NO: 1 or a homologous sequence thereof having at least 70% sequence identity.

In certain embodiments, the stem cell attracting factor is stromal cell-derived factor 1α (SDF-1α).

In certain embodiments, the stem cell attracting element retains no less than 60%, 70%, 80%, 90% or 95% of biological activity of a native SDF-1α.

In certain embodiments, the CBD is linked to the C-terminal of the SDF-1α.

In certain embodiments, the CBD is linked to the SDF-1α via a linker.

In certain embodiments, the linker is a polypeptide.

In certain embodiments, the linker has an amino acid sequence of SEQ ID NO: 2 or a homologous sequence thereof having at least 70% sequence identity.

In certain embodiments, the fusion protein has an amino acid sequence of SEQ ID NO: 9 or a homologous sequence thereof having at least 70% sequence identity. In certain embodiments, the fusion protein has an amino acid sequence of SEQ ID NO: 4 or a homologous sequence thereof having at least 70% sequence identity.

In certain embodiments, the matrix is a three-dimensional collagen scaffold.

In certain embodiments, the three-dimensional collagen scaffolds are porous.

In certain embodiments, the three-dimensional collagen scaffolds have at least 50% to 90% of porosity.

In certain embodiments, the three-dimensional collagen scaffolds are in membrane form.

In certain embodiments, the stem cell attracting element can be released from the three-dimensional collagen scaffolds in a sustained manner.

In certain embodiments, the stem cell attracting element provided herein can be released from the tissue scaffolds in a sustained manner. In certain embodiments, about 50% of the stem cell attracting element provided herein is released from the tissue scaffolds over a time period of at least 9 days.

In certain embodiments, the tissue scaffolds comprise 1 μg-1,000 μg of the stem cell attracting element pre-loaded to the tissue scaffolds.

The present disclosure further provides fusion proteins comprising CBD linked to a stem cell attracting factor. In certain embodiments, the stem cell attracting factor is stromal cell-derived factor 1α (SDF-1α). In certain embodiments, the fusion proteins retain no less than 60%, 70%, 80%, 90% or 95% of biological activity of a native SDF-1α.

In certain embodiments, the CBD is derived from a collagenase. In certain embodiments, the CBD has a length of no more than 20 amino acid residues.

In certain embodiments, the CBD has an amino acid sequence of SEQ ID NO: 1 or a homologous sequence thereof having at least 70% sequence identity.

In certain embodiments, the CBD is linked to the C-terminal of the SDF-1α. In certain embodiments, the CBD is linked to the SDF-1α via a linker.

In certain embodiments, the fusion proteins comprise an amino acid sequence of SEQ ID NO: 9 or a homologous sequence thereof having at least 70% sequence identity. In certain embodiments, the fusion proteins comprise an amino acid sequence of SEQ ID NO: 4 or a homologous sequence thereof having at least 70% sequence identity.

The present disclosure further provides methods of mobilizing stem cells to a target tissue in a subject, comprising administering an effective amount of the fusion proteins to the target tissue. In certain embodiments, the stem cells are endogenous stem cells.

The present disclosure further provides methods of mobilizing stem cells to a target tissue in a subject, comprising introducing the tissue scaffolds provided herein to the target tissue. In certain embodiments, the stem cells are endogenous stem cells.

In certain embodiments, the target tissue is an injured tissue.

In certain embodiments, the target tissue is a cardiac tissue, brain tissue, spinal cord tissue, muscle tissue or skin tissue.

The present disclosure further provides methods of promoting repair and/or regeneration of an injured tissue in a subject in need thereof, comprising introducing the tissue scaffolds provided herein to the injured tissue.

The present disclosure further provides use of the fusion proteins provided herein in the manufacture of a medicament for mobilizing stem cells to a target tissue. The present disclosure further provides use of the tissue scaffolds provided herein in the manufacture of an implant for mobilizing stem cells to a target tissue.

The present disclosure further provides use of the fusion protein in the manufacture of a three-dimensional tissue scaffold comprising a stem cell attracting element releasably bound to a matrix.

The present disclosure further provides use of the fusion protein provided herein in the manufacture of a tissue scaffold comprising a three-dimensional collagen scaffold associated with the fusion protein. Also provided herein are uses of the tissue scaffold provided herein in the manufacture of an implant for treating myocardial infarction, brain injury, spinal cord injury, muscle injury or skin injury.

1A shows a schematic diagram of the structural elements of NAT-SDF-1α and CBD-SDF-1α, wherein a CBD is connected to the C-terminal of NAT-SDF-1α through a linker.

1B shows the bands of NAT-SDF-1α and CBD-SDF-1α identified by Tricine-SDS-PAGE.

1C shows the bands of NAT-SDF-1α and CBD-SDF-1α identified by Western blot using anti-(His) 6 monoclonal antibody.

1D shows the binding curves of NAT-SDF-1α and CBD-SDF-1α to collagen as measured by ELISA using a primary antibody against polyhistidine and an alkaline phosphatase-conjugated secondary antibody (1:10,000; Sigma-Aldrich).

1E shows the dissociation curves of NAT-SDF-1α and CBD-SDF-1α from collagen. Data were generated by Scatchard analysis from the data of FIG. 1D.

1F shows the controlled release curves of NAT-SDF-1α and CBD-SDF-1α from collagen.

Figure 2:
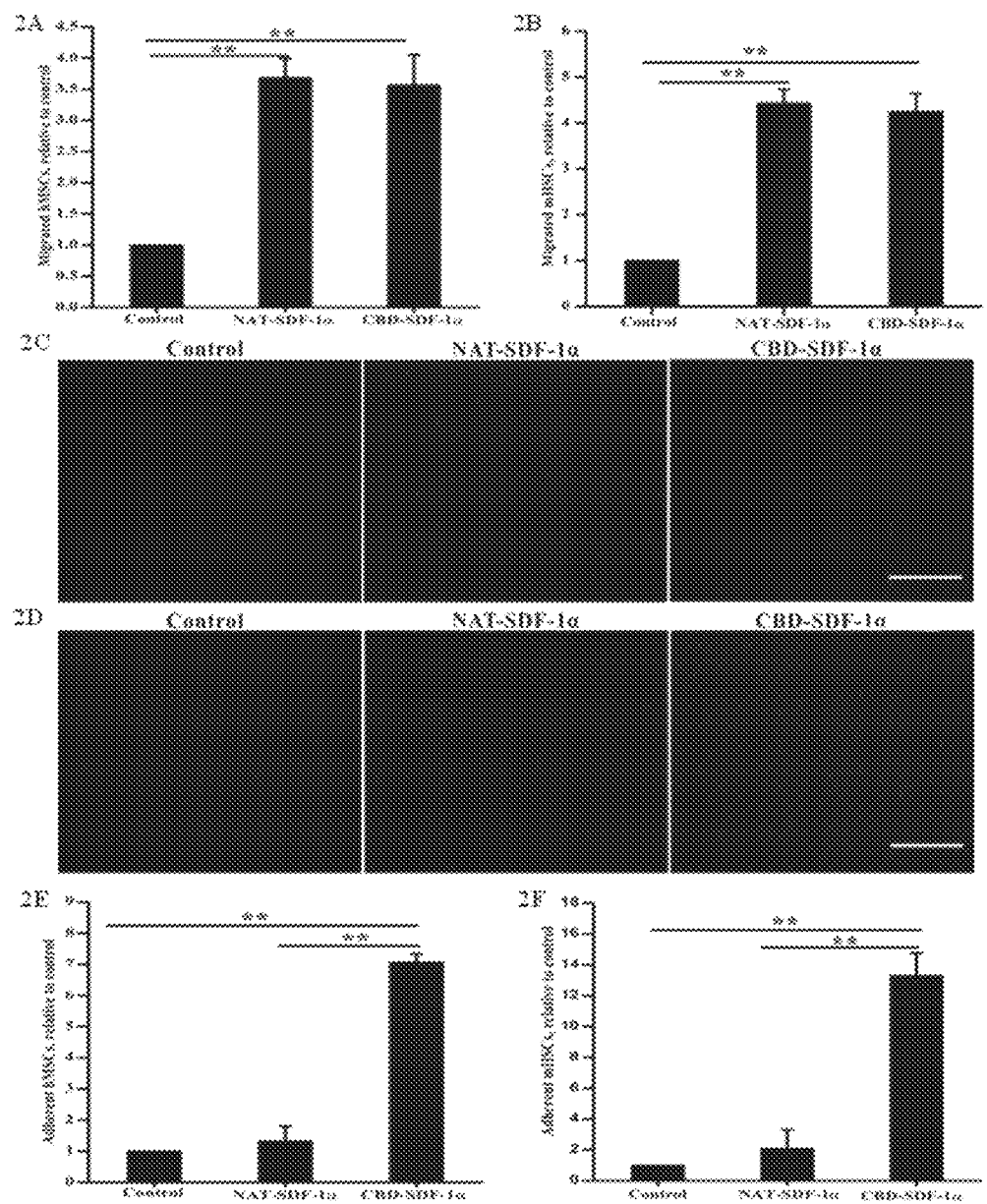

FIG. 2 shows the activity of NAT-SDF-1α and CBD-SDF-1α. Each assay was performed in triplicate wells. Data are presented as means±SEM, **P<0.01. Scale bar=100 μm.

2A shows the chemotaxis of human placenta-derived mesenchymal stem cells (hMSCs) in a modified Boyden chamber induced by chemokines. CBD-SDF-1α has similar chemotactic activity as NAT-SDF-1α, which means that the fusion of a collagen binding domain with SDF-1α did not affect the bioactivity of SDF-1α.

2B shows the chemotaxis of mouse c-kit positive (c-kit$^+$) hematopoietic stem cells (mHSCs) in a modified Boyden chamber induced by chemokines. CBD-SDF-1α has similar chemotactic activity as NAT-SDF-1α, which means that the fusion of a collagen binding domain with SDF-1α did not affect the bioactivity of SDF-1α.

2C shows the representative images of hMSCs retained on collagen gel treated with the control, NAT-SDF-1α and CBD-SDF-1α, respectively, under microscopy.

2D shows the representative images of mHSCs retained on collagen gel treated with the control, NAT-SDF-1α and CBD-SDF-1α, respectively, under microscopy.

2E shows the quantitative analysis of fold-changes of adherent hMSCs relative to control group.

2F shows the quantitative analysis of fold-changes of adherent mHSCs relative to control group.

Figure 3:
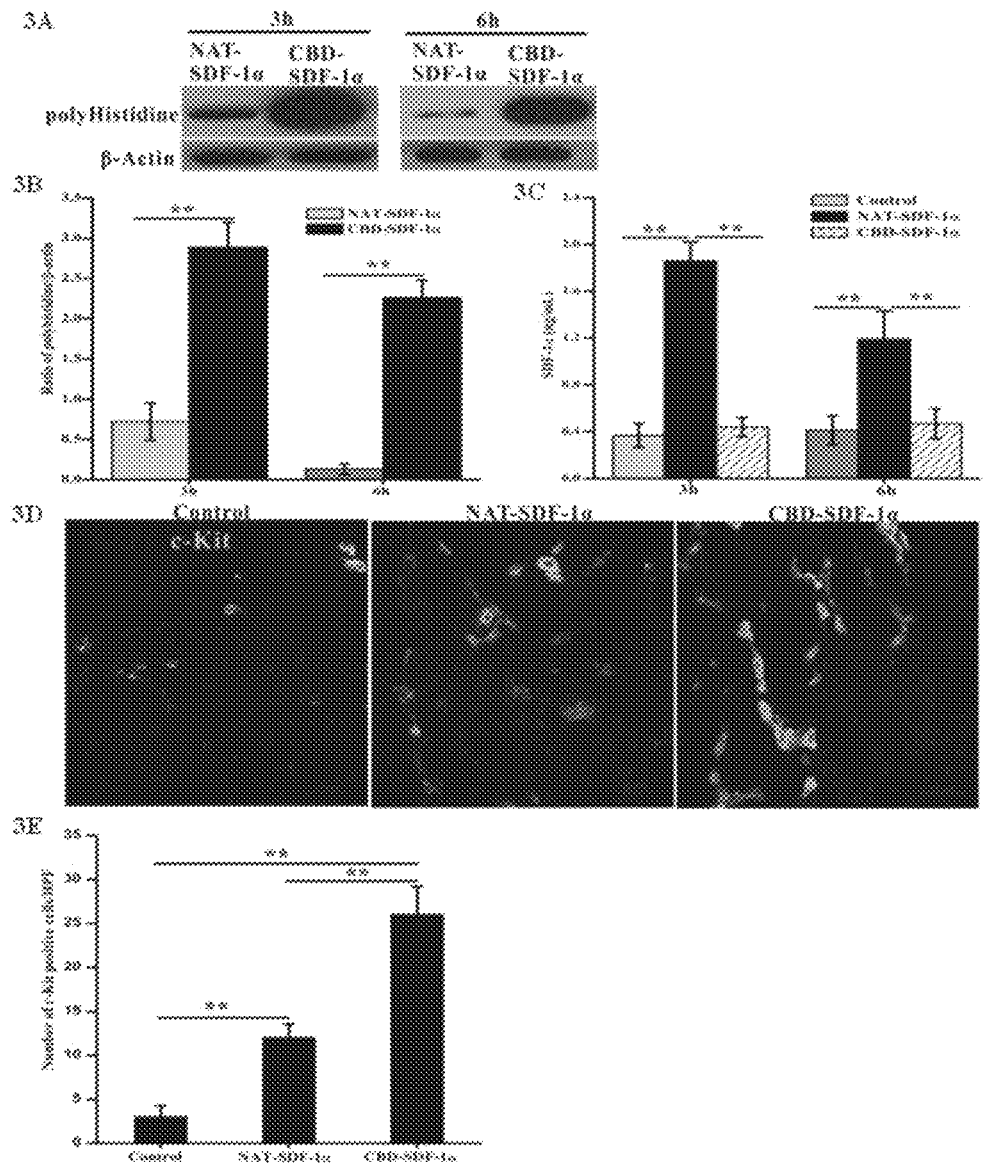

FIG. 3 shows the binding ability of NAT-SDF-1α and CBD-SDF-1α to the infarcted heart and recruitment of c-kit$^+$ stem cells in vivo. Data are presented as means±SEM, **P<0.01.

3A shows that at 3 or 6 h after injection of the NAT-SDF-1α or CBD-SDF-1α, Western blot was used to measure exogenous SDF-1α in the ischemic area with anti-polyhistidine antibody, and β-actin was used as internal control.

3B shows the quantification of the protein bands (n=6 in each group) of FIG. 3A.

3C shows the SDF-1α in serum were measured at 3 and 6 h after injection (n=6 in each group).

3D shows the representative images of c-kit$^+$ stem cells migrated to the ischemic area 4 days after surgery.

3E shows the average number of c-kit$^+$ cells in the infarcted heart (n=6 in each group). CBD-SDF-1α mobilized more c-kit$^+$ cells migrated to the infarcted heart.

Figure 4:
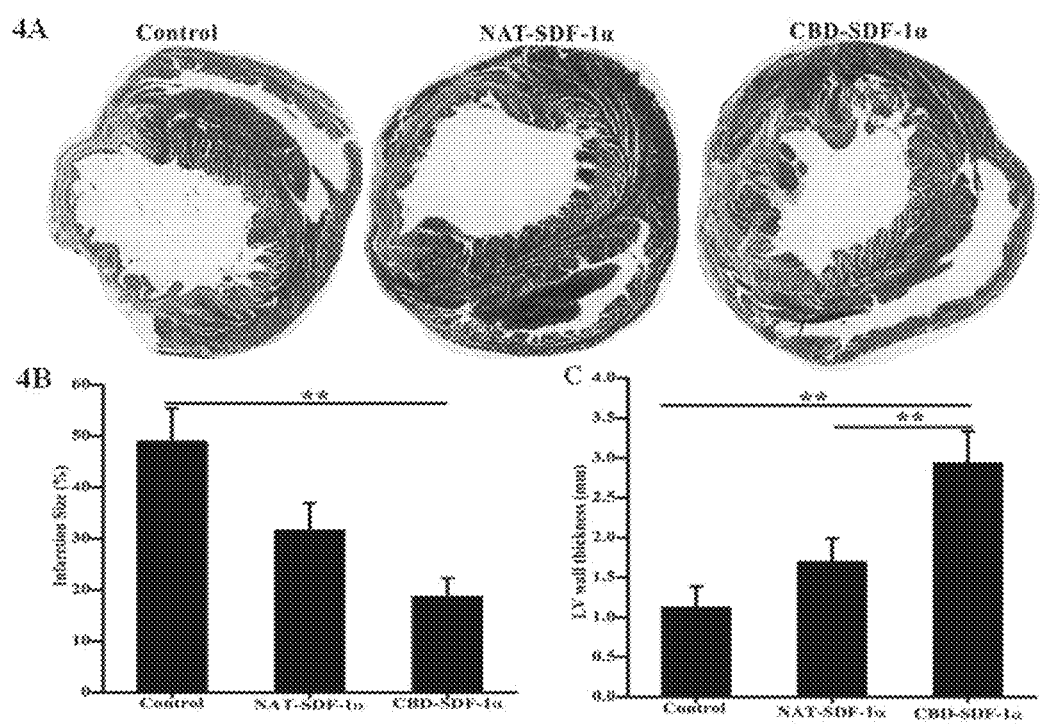

FIG. 4 shows the measurement of infarction size and left ventricle (LV) wall thickness. Data are presented as means±SEM, **P<0.01.

4A shows the representative images of Masson-trichrome staining.

4B shows the proportion of scar tissues (blue) in the left ventricle determined by calculating the ratio of the area of scar to the total area of the left-ventricular (n=8 in each group).

4C shows the average thickness of LV wall in the infarcted region (n=8 in each group). CBD-SDF-1α reduced infarction size and increased LV wall thickness.

Figure 5:
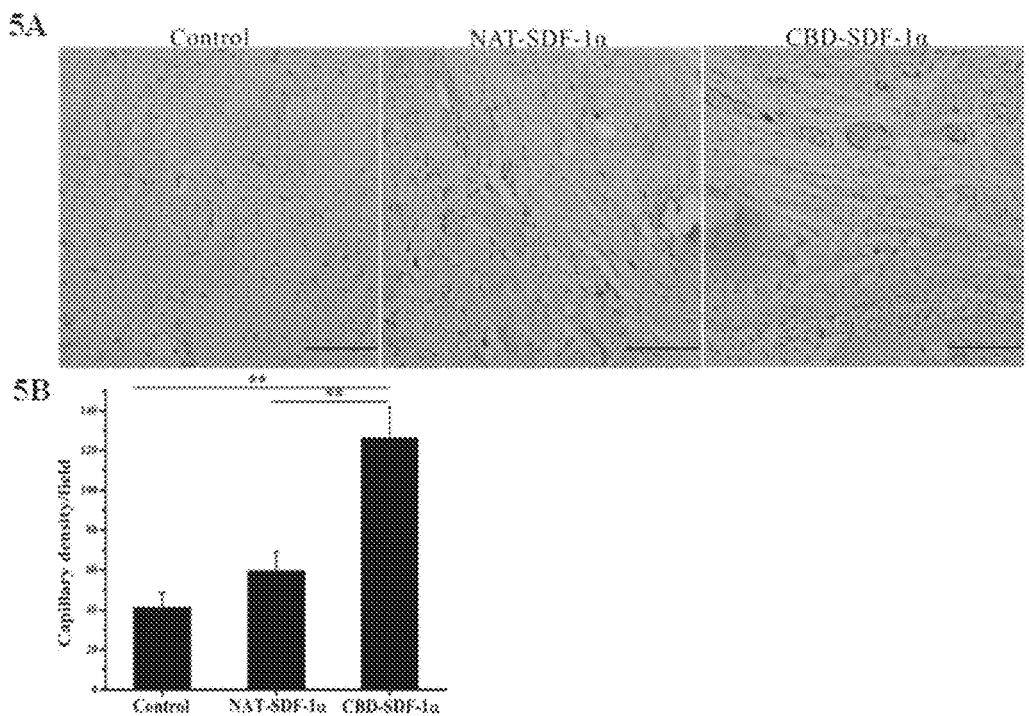

FIG. 5 shows the histological analysis of capillary density in the ischemic area using anti-Von Willebrand Factor (vWF) antibody. Data are presented as means±SEM, **P<0.01. Scale bar=50 μm.

5A shows the representative images of vWF staining of ischemic area treated with PBS (control group), NAT-SDF-1α and CBD-SDF-1α, respectively.

5B shows the average capillary density (n=8 in each group) of the treated samples and control samples, respectively. CBD-SDF-1α increased capillary density in the ischemic area.

Figure 6:
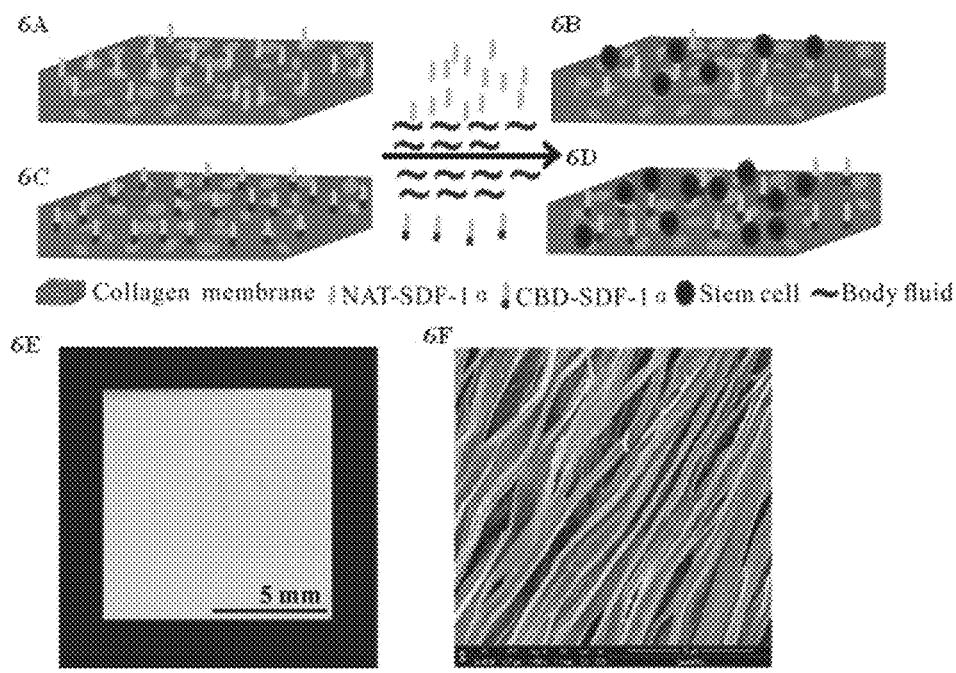

FIG. 6 shows the schematic diagram for construction of functionalized myocardial patch and image of collagen membranes.

NAT-SDF-1α in the collagen membrane (6A) diffuses from the collagen membrane quickly into body fluid and recruits few stem cells (6B), while CBD-SDF-1α can bind to the collagen membrane (6C) and recruit more stem cells (6D).

6E shows the macroscopic image of collagen membrane.

6F shows the SEM image of morphology of collagen membrane.

Figure 7:
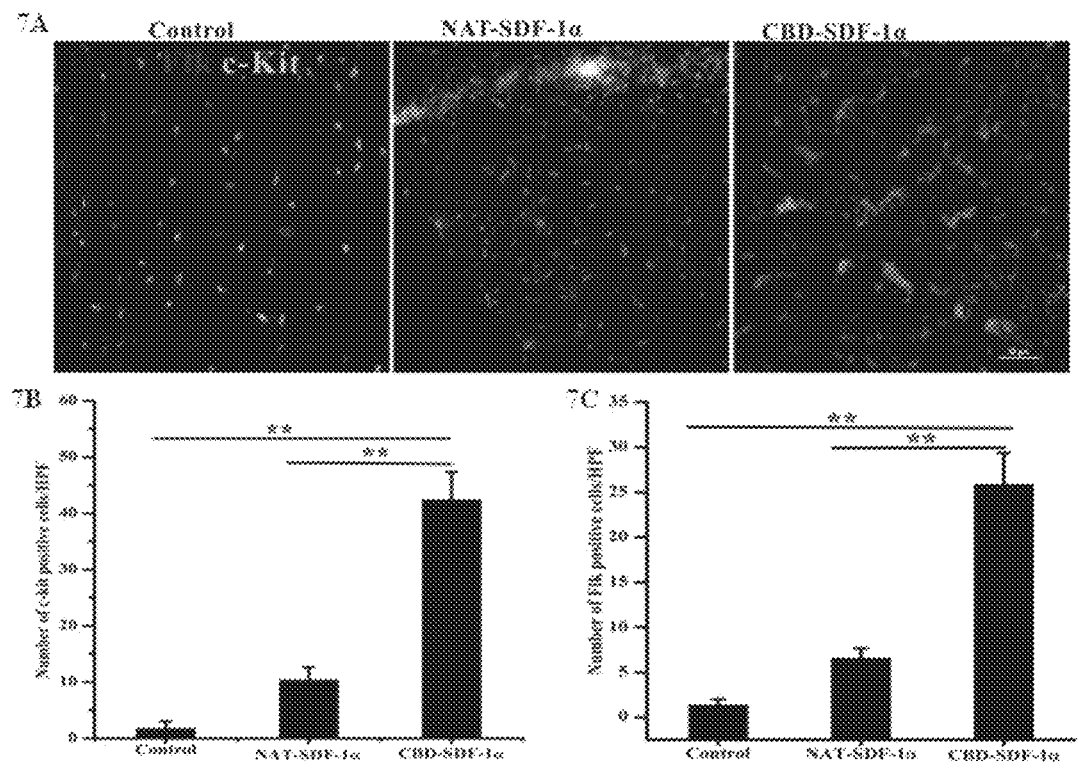

FIG. 7 shows the endogenous stem cells recruited by the CBD-SDF-1α modified collagen membrane. Data are presented as means±SEM, **P<0.01.

7A shows the representative immunofluorescent images of c-kit (green), Flk (red), and DAPI (blue) staining of samples treated with collagen membranes pre-loaded with nothing (blank control), NAT-SDF-1α and CBD-SDF-1α, respectively.

7B shows the quantitative analysis of average number of c-kit$^+$ cells.

7C shows the quantitative analysis of average number of Flk$^+$ cells.

Figure 8:
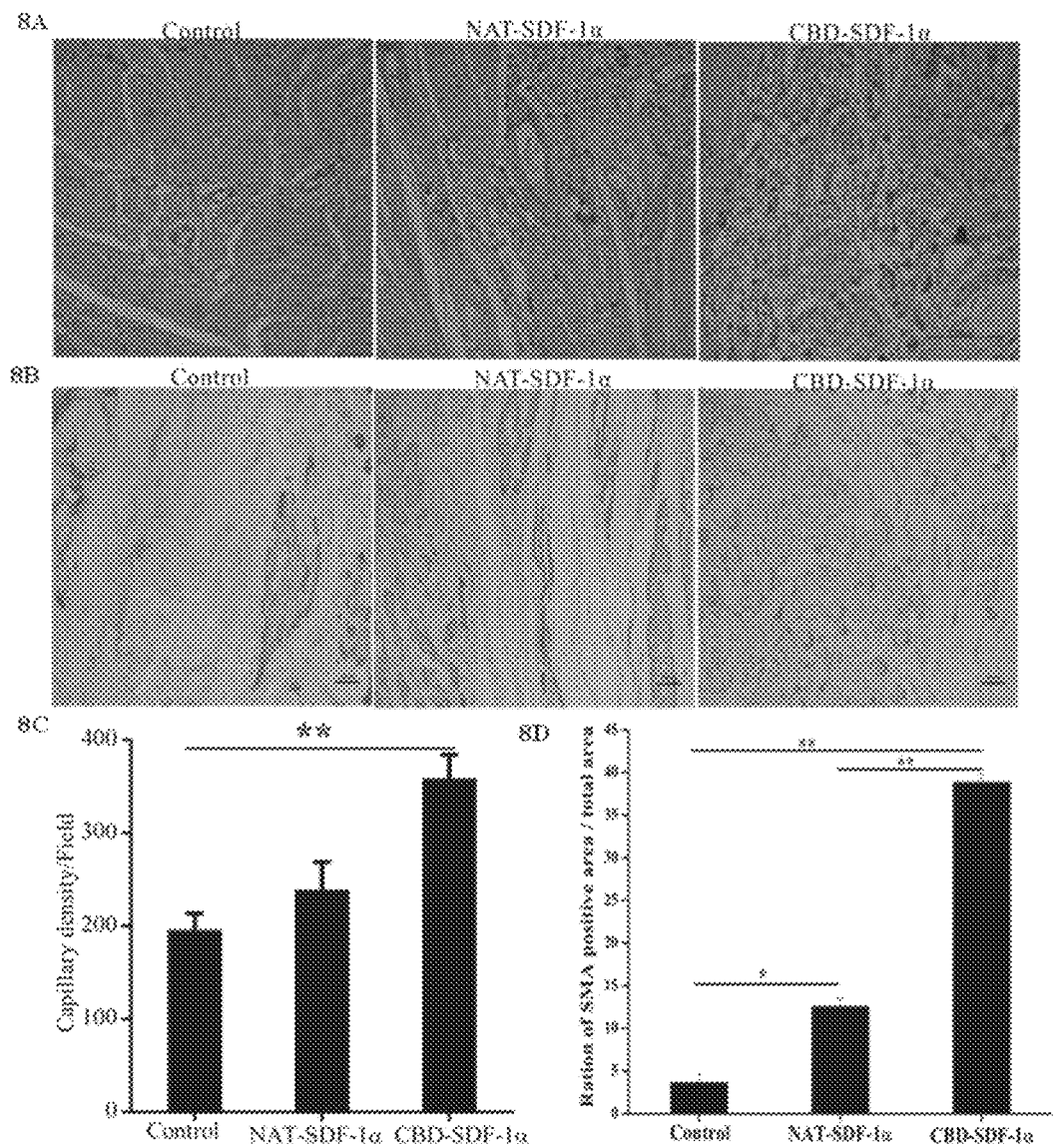

FIG. 8 shows the histological analysis of capillary density and α-SMA (sarcomeric actin)-positive cells in collagen membrane. Data are presented as means±SEM. *P<0.05, **P<0.01.

8A shows the vWF antibody detected capillary density in collagen membrane treated samples. Capillary density in the CBD-SDF-1α-treatment group was higher than that of control and NAT-SDF-1α.

8B shows the α-SMA antibody was used to detect cardiomyocytes in samples treated with collagen membranes pre-loaded with nothing (blank control) NAT-SDF-1α and CBD-SDF-1α, respectively. Collagen membrane pre-loaded with CBD-SDF-1α promoted the regeneration of myocardium.

8C shows the quantification of capillary density.

8D shows the percentage of α-SMA positive area in total area, n=8 in each group.

Figure 9:
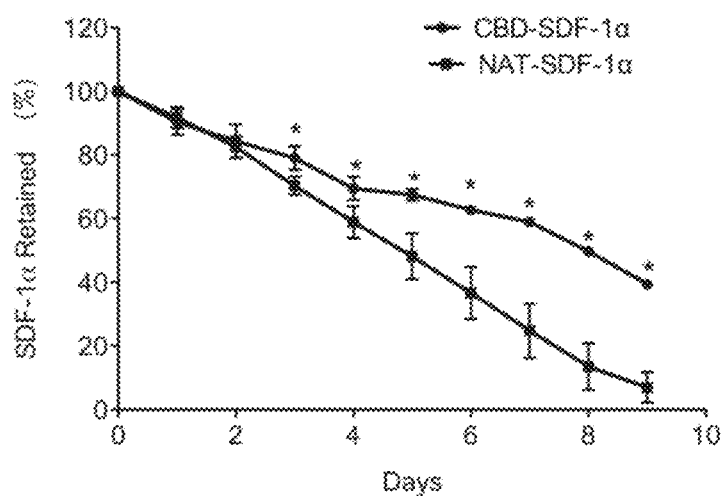

FIG. 9 shows the controlled release curves of NAT-SDF-1α and CBD-SDF-1α from 3D collagen membrane scaffolds. Data are presented as mean±SEM, *p<0.05.

FIG. 10 shows the amino acid sequences and corresponding nucleic acid sequences of CBD (SEQ ID NOs: 1 and 5), linker (SEQ ID NOs: 2 and 6), SDF-1α (SEQ ID NOs: 3 and 7), the CBD-SDF-1α fusion proteins with (SEQ ID NOs: 4 and 8) and without (SEQ ID NOs: 9 and 10) His-tag (6×His flanked with amino acids or nucleotides derived from the pET28a vector), respectively.

DETAILED DESCRIPTION OF THE INVENTION

The present disclosure provides stem cell attracting elements, and tissue scaffolds comprising the stem cell attracting elements releasably bound to a matrix (such as collagen matrix), and methods of using such stem cell attracting elements and such tissue scaffolds.

Stem Cell Attracting Elements

In one aspect, the present disclosure provides a stem cell attracting element comprising a stem cell attracting factor linked to a binding moiety capable of being releasably bound to a matrix.

The present disclosure may include any stem cells that can promote tissue repair and/or regeneration. Examples of stem cells include, hematopoietic stem cells (which are self-renewing, multipotent bone marrow cells capable of giving rise to blood cells such as leukocytes, erythrocytes and platelets), endothelial progenitor cells (which contributes to new blood vessel formation), mesenchymal stem cells (which are multipotent, non-hematopoietic stromal cells that are found in various adult tissues and are capable of differentiating in various cells of mesenchymal lineages such as bone, muscle, cartilage and adipose cells), neuronal stem cell (which are self-renewing and multipotent, allowing cell replacement therapies for diseases in the nervous system, capable of differentiating into neurons, astrocytes, and oligodendrocytes) and cardiac stem cells (which are self-renewing, clonogenic, and multipotent, capable of giving rise to cells such as myocytes, smooth muscle, and endothelial cells).

The term "stem cell attracting factor" as used herein can be any molecule that can attract stem cells to migrate to accumulate around it and can be peptides/proteins, and active fragments or analogs thereof, or alternatively can also be chemical compounds such as small molecule compounds. Examples of stem cell attracting factor include, but not limited to, stromal cell-derived factor-1α (SDF-1α) (e.g. native SDF-1α, and protease-resistant SDF-1α (Segers V F et al., Local delivery of protease-resistant stromal cell derived factor-1 for stem cell recruitment after myocardial infarction, Circulation. 2007; 116(15):1683-1692), Diprotin A (Zhang D et al., Genetically manipulated progenitor cell sheet with diprotin A improves myocardial function and repair of infarcted hearts, Am J Physiol Heart Circ Physiol. 2010 November; 299(5):H1339-1347), Hepatocyte growth factor (HGF) (Shen C. et al., Conditioned medium from umbilical cord mesenchymal stem cells induces migration and angiogenesis, Mol Med Rep. 2015; 12(1):20-30), Monocyte chemotactic proteins (MCPs, for example, MCP-1 (Belema-Bedada F et al., Efficient homing of multipotent adult mesenchymal stem cells depends on FROUNT-mediated clustering of CCR2, Cell Stem Cell. 2008; 2(6):566-575.), MCP-3, MCP-5), Matrix metalloproteinase-2 (MMP-2) (Bhoopathi P. et al., MMP-2 mediates mesenchymal stem cell tropism towards medulloblastoma tumors, Gene Ther. 2011; 18(7):692-701), Galanin, Jagged (Kwon S M, et al., Specific Jagged-1 signal from bone marrow microenvironment is required for endothelial progenitor cell development for neovascularization, Circulation. 2008; 118(2):157-165.), Notch (Li Y, et al., Notch1 in bone marrow-derived cells mediates cardiac repair after myocardial infarction, Circulation. 2011; 123(8):866-876.), vascular endothelial growth factor (VEGF) (Tang J. et al., Vascular endothelial growth factor promotes cardiac stem cell migration via the PI3K/Akt pathway, Exp Cell Res. 2009; 315(20):3521-31), epidermal growth factor (EGF) (GAO Z. Q. et al., The Effect of Epidermal Growth Factor on Chemotaxis of Bone Marrow Mesenchymal Stem Cells in Vitro, Progress of Anatomical Sciences. 2008; 03), transmembrane protein 18 (Jurvansuu J. et al., Transmembrane protein 18 enhances the tropism of neural stem cells for glioma cells, Cancer Res. 2008 Jun. 15; 68(12):4614-4622), glioma-produced ECM (tenascin-C) (Ziu M. et al., Glioma-produced extracellular matrix influences brain tumor tropism of human neural stem cells, J Neurooncol. 2006 September; 79(2):125-133), stem cell factor (SCF) (Liu Y. et al., Tropism of Bone Marrow Mesenchymal Stem Cells in Neuroblast Differentiation for Stem Cell Factor, Suzhou University Journal of Medical Science. 2010; 04), PDGF and IGF-1 (Mishima Y et al., Chemotaxis of human articular chondrocytes and mesenchymal stem cells, J Orthop Res. 2008; 26(10):1407-1412).

The term "binding moiety" as used herein refers to a moiety or molecule or fragment which can specifically associate or bind to a matrix. Suitable binding moieties can be, for example, a binding domain of a peptide/protein, a chemical compound, an antigen or antibody, a nucleic acid fragment, and the like.

The binding moiety is capable of being releasably bound to a matrix. The term "releasably bound" or "releasably bind" as used herein means the binding moiety of the stem cell attracting element can bind to the matrix through one or more non-covalent bonds which permit the stem cell attracting element to be released from the matrix when being subjected to a condition for release.

Binding moiety can be selected as appropriate by people skilled in the art, as long as its linkage to the stem cell attracting factor does not significantly reduce the biological activity of the latter (or in other words, the resulting stem cell attracting element retains sufficient activity in stem cell attraction), and provides a required release profile under a specified release condition.

In certain embodiments, the binding moiety is collagen binding domain (CBD), and the matrix comprises collagen. In certain embodiments, the binding moiety is laminin binding domain (LBD) or fibrogen binding domain (FBD), and the matrix is laminin or fibrogen.

"Collagen binding domain" or "CBD" as used herein refers to a peptide fragment or domain which is capable of specific binding to collagen. CBD can be derived from proteins that specifically bind to collagen, for example, collagenase, collagen receptor, or anti-collagen antibody. Exemplary collagen-binding proteins include, without limitation, integrin α1β1, integrin α2β1, integrin α10β1, integrin α11β1, discoidin domain receptor (DDR) 1, DDR2, Glycoprotein VI, C-proteinase, fibronectin, interleukin-2, matrix metalloproteases 1, 2, 9, and 13, phosphophoryn, thrombospondin, biglycan, bilirubin, BM40/SPARC, MRP8, MRP-14, calin from leeches, fibromodulin, Gla protein, glycoprotein 46, heat shock protein 47, lumican, myelin associated glycoprotein, platelet receptors, *staphylococcus aureus* surface molecules and other microbial adhesion molecules, *Clostridium histolyticum* collagenase, syndecan-1, tenascin-C, vitronectin, von Willebrand factor, and factor XII (see, for more details, Di Lullo, G A., et al. Mapping the ligand-binding sites and disease-associated mutations on the most abundant protein in the human, type I collagen. J Biol Chem. 2002; 277(6): 4223-4231).

In certain embodiments, CBD is derived from collagenase. Collagenase is a family of enzymes that degrade collagen. Suitably CBD of a collagenase is only a portion of a collagenase which retains the binding capability to collagen but lacks collagenase activity. Different types of collagenase are known in the art, for example, bacterial collagenase, animal collagenase, and so on.

Examples of bacterial collagenase include, for example, such as *Clostridium histolyticum* ColH (see, e.g., GenBank Accession No. D29981.1), *Clostridium histolyticum* ColG (see, e.g., Matsushita O. et al., Gene duplication and multiplicity of collagenases in *Clostridium histolyticum*, J. Bacteria. 1999; 181:923-933), and Cna from *Staphylococcus aureus* (see, e.g. Deivanayagam C. C. et al., Novel fold and assembly of the repetitive B region of the *Staphylococcus aureus* collagen-binding surface protein, Structure, 2000; 8(1):67-78).

Examples of animal collagenase include, such as matrix metallopeptidase 1 with GenBank Accession No. ACH91675.1, ACH91676.1, BAG72620.1, AES02042.1, ACC61049.1, NP_001025501.1, XP_005911941.1, ABM84830.1, ABM81655.1, JAA13625.1, JAA01146.1, EAW67031.1, AAH13875.1, EDL24934.1, NP_001128002.1, AAI48745.1, AAI46302.1, EDL00990.1, AAI17757.1 (also named as interstitial collagenase), and matrix metallopeptidase 8 with GenBank Accession No. EDL78530.1, EDL24937.1, AAH42742.1, AES02057.1, AES02056.1, NP_001088503.1, EAW67027.1, AAH74988.1, AAH74989.1 (also named as neutrophil collagenase). GenBank Accession Numbers and associated sequence information obtainable through databases such as National Center for Biotechnology Information (NCBI) and other data referred to throughout the disclosure herein are incorporated by reference for the portions of the document discussed herein, as well as in their entirety.

Various CBD have been identified from the collagen-binding proteins, see, for example, U.S. Patent Publication Nos. 2004/0053368, 2015/0202350, and 2015/0038423. CBD can be obtained using methods known in the art such as expression by natural or recombinant host cells and purification using standard techniques, chemical synthesis, for example, solid-phase peptide synthesis, etc.

In certain embodiments, CBD has a length of no more than 20 amino acid residues, or preferably no more than 19, 18, 17, 16, 15, 14, 13, 12, 11, 10, 9, 8, or 7 amino acid residues.

In certain embodiments, CBD comprises an amino acid sequence of SEQ ID NO: 1 (see FIG. 10) or a homologous sequence thereof having at least 70% sequence identity, provided that the homologous sequence has similar collagen binding activity as that of SEQ ID NO: 1. In certain embodiments, CBD comprises an amino acid sequence of SEQ ID NO: 1 or a homologous sequence thereof having at least 95% sequence identity, or at least 90% sequence identity, provided that the homologous sequence has similar collagen binding activity as that of SEQ ID NO: 1.

"Percent (%) sequence identity" with respect to a target protein is defined as the percentage of amino acid residues in a sequence of interest that are identical with the amino acid residues in the target protein, after aligning the sequences and introducing gaps, if necessary, to achieve the maximum percent sequence identity, and not considering any conservative amino acid substitutions as part of the sequence identity. Alignment for purposes of determining the percentage of amino acid sequence identity can be achieved in various ways that are within the skill in the art, for instance, using publicly available computer software such as BLAST, BLAST-2, ALIGN or Megalign (DNASTAR) software. See, for example, Altschul S. F. et al., Gapped BLAST and PSI-BLAST: a new generation of protein database search programs, Nucleic Acids Res. 1997; 25:3389-3402; Altschul S. F. et al., Local alignment statistics, Methods in Enzymology. 1996; 266:460-480. Those skilled in the art can determine appropriate parameters for measuring alignment, including any algorithms needed to achieve maximal alignment over the full length of the sequences being compared.

The term "stem cell attracting element" as used herein refers to any conjugate molecule that includes a stem cell attracting factor and a binding moiety, and that can promote the attraction, recruitment, and/or migration of stem cells. A stem cell attracting element may be a protein or a peptide covalently linked to a moiety which is not a peptide, for example, a chemical compound or a nucleic acid molecule.

In certain embodiments, the stem cell attracting element is a fusion protein comprising stem cell attracting factor linked to the CBD. "Fusion protein" as used herein refers to a chimeric protein in which at least two different amino acid sequences derived from separate proteins/peptides are covalently linked together as one protein/peptide.

In certain embodiments, the stem cell attracting factor is SDF-1α. SDF-1α is a chemokine capable of binding to its receptor C—X—C chemokine receptor type 4 (CXCR4). CXCR4 is expressed on stem cells such as hematopoietic stem cells, and mediates the stem cells to migrate in response to the concentration gradient of SDF-1.

In certain embodiments, the SDF-1α is native human SDF-1α.

In certain embodiments, the native human SDF-1α comprises the amino acid sequence of SEQ ID NO: 3 (see FIG. 10), or a homologous sequence thereof having at least 70%, at least 80%, at least 85%, at least 90%, or at least 95% sequence identity to the amino acid sequence of SEQ ID NO: 3, provided that the homologous sequence has similar biological activity (e.g. inducing $CXCR4^+$ stem cell migration) as that of SEQ ID NO: 3. In certain embodiments, the stem cell attracting factor retains no less than 60%, 70%, 80%, 90% or 95% of biological activity of a native human SDF-1α in attracting stem cells.

In certain embodiments, the CBD is linked to the C-terminal of the SDF-1α. CBD can be linked either directly or indirectly to SDF-1α. In certain embodiments, CBD is linked to SDF-1α via a linker. In certain embodiments, the linker is a polypeptide linker comprising an amino acid sequence of SEQ ID NO: 2 (see FIG. 10) or a homologous sequence thereof having at least 70% sequence identity, or at least 80% sequence identity, or at least 90% sequence identity to the amino acid sequence of SEQ ID NO: 2. In certain embodiments, the linker is a bi-functional cross-linker such as disuccinimidyl glutarate, or 1-ethyl-3-[3-dimethylaminopropyl] carbodiimide hydrochloride), which can link at one end the amino group of a first polypeptide and at the other end the carboxyl end of a second polypeptide. A skilled artisan can select a suitable linker from those known in the art, as long as the linked fusion protein retains sufficient biological activities of both CBD and SDF-1α.

In certain embodiments, the fusion protein comprises an amino acid sequence of SEQ ID NO: 9 (see FIG. 10), or a homologous sequence thereof having at least 70% sequence identity, provided that the homologous sequence has similar activity as the sequence of SEQ ID NO: 9 both in terms of collagen binding and SDF-1α biological activity.

In certain embodiments, the fusion protein may optionally comprise a protein tag. Protein tags are widely used in the art to, for example, facilitate purification and/or antibody detection of a recombinant protein. Various protein tags have been used and are generally believed as not inactivating the protein to which it is fused. Examples of protein tags include, poly(His) tag, Myc-tag, HA-tag, FLAG-tag, chitin binding protein tag, glutathione-S-transferase tag, and so on.

In certain embodiments, the fusion protein further comprises a protein tag and comprises an amino acid sequence of SEQ ID NO: 4, which differs from SEQ ID NO: 9 in a protein tag at the N-terminal.

In certain embodiments, the fusion protein retains no less than 60%, 70%, 80%, 90% 95%, 99% of the biological activity of a native SDF-1α. In certain embodiments, the fusion protein retains no less than 95% of the biological activity of a native SDF-1α. In certain embodiments, the fusion protein retains all biological activity of a native SDF-1α. The term "native" SDF-1α as used herein refers to a SDF-1α having an amino acid sequence that exists in a naturally occurring SDF-1α, for example, the SDF-1α consisting of an amino acid sequence of SEQ ID NO: 3. Native SDF-1α can be either isolated from a biological sample (e.g. blood or serum), or recombinantly expressed followed by purification.

Biological activity of a native SDF-1α can include, for example, activation of its receptor CXCR4 to induce intracellular signaling that initiates signals related to chemotaxis of CXCR4-expressing cells, cell survival and/or proliferation, increase in intracellular calcium, and gene transcription (Teicher B. A. and Fricker S. P., CXCL12 (SDF-1)/CXCR4 pathway in cancer, Clin. Cancer Res. 2010; 16(11): 2927-31.). Activation of CXCR4 can be determined based on the receptor signaling, using assays known in the art, for example, by calcium flux assay (see, for example, Princen K. et al., Evaluation of SDF-1/CXCR4-induced Ca2+ signaling by fluorometric imaging plate reader (FLIPR) and flow cytometry, Cytometry A. 2003; 51(1):35-45) which detects the flux of intracellular calcium resulting from activation of CXCR4 receptor. To determine chemotaxis of CXCR4-expressing cells, chemotaxis assay can be used (see, for example, Chen H C et al., Boyden chamber assay, Methods in Molecular Biology, 2005; 294: 15-22) which involves placing CXCR4-expressing cells in an upper chamber and detect their ability to migrate across a permeable membrane to the lower chamber filled with SDF-1α-containing fluid. In certain embodiments, the fusion protein retains no less than 60%, or no less than 70%, or no less than 80%, or no less than 90%, or no less than 95% of the activity of a native SDF-1α in attracting stem cells.

The fusion protein is capable of collagen binding. Collagen binding activity can be determined by assays such as ELISA, or by surface plasmon resonance assay (e.g. using Biacore techniques), or by flow-through collagen binding assays as previously described in U.S. Patent Publication No. 2010/0129341 or U.S. Patent Publication No. 2013/0337017A1, which are incorporated herein by reference in its entirety, or any other suitable methods known in the art to determine the collagen binding activity. In certain embodiments, the fusion protein has a collagen binding affinity (Kd value) of no more than 10 μM, 9 μM, 7 μM, 6 μM, 5 μM, 4 μM, 3 μM, 2 μM, 1 μM, 0.8 μM, 0.7 μM, 0.5 μM, 0.4 μM, or 0.3 μM, as determined by ELISA assay. In certain embodiments, the fusion protein has a collagen binding affinity of no more than 0.5 μM as determined by ELISA assay. Kd value can be calculated as the ratio of dissociation rate to association rate ($k_{off}/k_{on}$) when the binding between the fusion protein and collagen reaches equilibrium. In certain embodiments, the Kd value can be calculated by the Scatchard analysis (Munson P J and Rodbard D. Ligand: a versatile computerized approach for characterization of ligand-binding systems, Anal Biochem. 1980; 107(1): 220-39). Kd value can also be determined using other suitable methods such as surface plasmon resonance binding assay using instruments such as Biacore (see, for example, Murphy, M. et al, Current protocols in protein science, Chapter 19, unit 19.14, 2006).

Methods and Materials for Producing the Fusion Protein

In one aspect, the fusion protein provided herein can be produced by recombinant methods. Basically, polynucleotide encoding the fusion protein provided herein can be isolated and inserted to a vector for amplification or expression. The term "vector" as used herein refers to a nucleotide vehicle into which a polynucleotide encoding a protein may be operably inserted so as to bring about the expression of that protein. The vector comprising the polynucleotide encoding the fusion protein may be used to transform, transduce, or transfect a host cell so as to bring about expression of the fusion protein by the host cell.

Polynucleotides encoding the fusion protein can be obtained by people in the art without undue burden. For example, polynucleotides encoding SDF-1α can be obtained using reverse transcriptase PCR using a primer that specifically amplifies the encoding sequence of SDF-1α. CBD sequence can also be obtained by people in the art, for example, based on the amino acid sequence of CBD, people in the art can readily identify the corresponding encoding sequence for the CBD from publicly available database such as NCBI, and obtain the coding polynucleotide by, e.g., reverse transcriptase PCR or DNA synthetic methods. Where applicable, the linker sequence can also be obtained through PCR or artificial DNA synthesis. The polynucleotide sequence encoding SDF-1α, CBD and optionally the linker may be engineered to contain matching restriction sites and accordingly can be ligated together using a suitable ligase. Exemplary polynucleotide sequences encoding CBD, linker and SDF-1α are provided in SEQ ID NOs: 5-7 (see FIG. 10), and exemplary polynucleotide sequence encoding the fusion protein is provided in SEQ ID NO: 8 or 10 (see FIG. 10).

Many vectors are known in the art to express an interested protein. An expression vector generally includes, but is not limited to, one or more components of the following: a signal sequence, an origin of replication, one or more marker genes, an enhancer element, a promoter, and a transcription termination sequence.

Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40).

The fusion protein can be expressed in suitable host cells, for example prokaryotes, eukaryotic microbes, plant cells, insect cells, and vertebrate cells.

Examples of prokaryotes include, Gram-negative or Gram-positive organisms, for example, Enterobacteriaceae such as *Escherichia*, e.g., *E. coli, Enterobacter, Erwinia*,

*Klebsiella, Proteus, Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

Suitable eukaryotic microbes include, for example, filamentous fungi or yeast. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Plant cells and insect cells can also be used to express the fusion protein. Plant cell cultures of cotton, corn, potato, soybean, *petunia*, tomato, and tobacco can also be utilized as hosts.

Examples of vertebrate cells include, monkey kidney CV1 line transformed by SV40 (COS-7, ATCC CRL 1651); human embryonic kidney line (293 or 293 cells subcloned for growth in suspension culture, Graham F. L. et al., Characteristics of a human cell line transformed by DNA from human adenovirus type 5, J. Gen Virol. 1977; 36(1): 59-74); baby hamster kidney cells (BHK, ATCC CCL 10); Chinese hamster ovary cells/-DHFR (CHO, Urlaub G et al., Isolation of Chinese hamster cell mutants deficient in dihydrofolate reductase activity, Proc. Natl. Acad. Sci. USA, 1980; 77:4216-4220); mouse sertoli cells (TM4, Mather J. P., Establishment and characterization of two distinct mouse testicular epithelial cell lines, Biol. Reprod. 1980; 23:243-252); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather J. P. et al., Culture of testicular cells in hormone-supplemented serum-free medium, Annals N.Y. Acad. Sci. 1982; 383:44-68); MRC 5 cells; FS4 cells; and a human hepatoma line (Hep G2).

Host cells are transformed with the above-described expression or cloning vectors for production of polypeptide of the present application and cultured in conventional nutrient media modified as appropriate for inducing promoters, selecting transformants, or amplifying the genes encoding the desired sequences.

The host cells used to produce polypeptides of the present application may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham R. G et al., Media and growth requirements, Meth. Enz. 1979; 58:44-93, Barnes D. et al., Methods for growth of cultured cells in serum-free medium, Anal. Biochem. 1980; 102:255-270, U.S. Pat. No. 4,767,704; 4,657,866; 4,927,762; 4,560,655; or 5,122,469; WO 90/03430; WO 87/00195; or U.S. Pat. No. RE30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as ampicillin, neomycin, methotrexate, tetracycline, or gentamycin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The fusion proteins of the present application can also be produced by chemical synthesis, for example, the solid phase synthesis method described by Merrifield R. B., Solid Phase peptide synthesis. I. The synthesis of a tetrapeptide, J. Am. Chem. Soc. 1963; 85: 2149-2154 or the standard solution synthesis method described in "Peptide Synthesis" by Bodanszky, et al, second edition, John Wiley and Sons, 1976. These books are entirely incorporated herein by reference.

The general procedure of the solid phase method of synthesis of a protein involves initially attaching the protected C-terminal amino acid of the protein to the resin. After attachment the resin is filtered, washed and the protecting group (e.g. t-butyloxycarbonyl) on the alpha amino group of the C-terminal amino acid is removed. The removal of this protecting group must take place, of course, without breaking the bond between that amino acid and the resin. To the resulting resin peptide is then coupled the penultimate C-terminal protected amino acid. This coupling takes place by the formation of an amide bond between the free carboxy group of the second amino acid and the amino group of the first amino acid attached to the resin. This sequence of events is repeated with successive amino acids until all amino acids of the peptide are attached to the resin. Finally, the protected protein is cleaved from the resin and the protecting groups removed to obtain the desired peptide. The cleavage techniques used to separate the peptide from the resin and to remove the protecting groups depend upon the selection of resin and protecting groups and are known to those familiar with the art of peptide synthesis.

The resin mentioned above may be any suitable polymer and shall contain a functional group to which the first protected amino acid can be firmly linked by a covalent bond. Various polymers are suitable for this purpose, such as cellulose, polyvinyl alcohol, polymethylmethacrylate, and polystyrene. Appropriate protecting groups usable in solid phase synthesis include t-butyloxycarbonyl (BOC), benzyl (BZL), t-amyloxycarbonyl (AOC), tosyl (TOS), o-bromophenylmethoxycarbonyl (BrZ), 2,6-dichlorobenzyl (BZLCl$_2$), and phenylmethoxycarbonyl (Z or CBZ). Additional protecting groups are also described in J. F. W. McOmie, "Protective Groups in Organic Chemistry", Plenum Press, New York, 1973. This book is entirely incorporated herein by reference.

The standard solution synthesis method can be performed by either stepwise or block coupling of amino acids or peptide fragments using chemical or enzymatic methods of amide bond formation. These solution synthesis methods are well known in the art (see E. Schroder and K. Kubke, The Peptides, Vol. 1, Academic Press, New York, 1965; Sambrook, Fritsch & Maniatis, Molecular Cloning: A laboratory Manual, 2nd Edition, Cold Spring Harbor Laboratory, 1989).

The fusion protein of the present application may be recovered after the expression or production. When using recombinant techniques, a fusion protein of the present application can be produced intracellularly, in the periplasmic space, or directly secreted into the medium. Fusion proteins of the present application may be recovered from culture medium or from host cell lysates. If membrane-bound, it can be released from the membrane using a suitable detergent solution (e.g. Triton-X 100) or by enzymatic cleavage. Cells employed in expression of a fusion protein of the present application can be disrupted by various physical or chemical means, such as freeze-thaw cycling, sonication, mechanical disruption, or cell lysing agents.

If a fusion protein is chemically synthesized, the fusion protein of the present application may be recovered from the reaction medium by any suitable techniques capable of separating the desired peptide from other components in the medium. For a solid phase synthesis, the protected fusion protein is firstly cleaved off the resin using a suitable cleaving solution. The selection of cleaving solution depends upon the properties of the resin and the amino acid bound thereto (such as trifluoroacetic acid for FMOC method). Cleaving is usually carried out under acid condition. Upon completion of cleaving, a dissociative fusion protein is then obtained and further purified using any suitable techniques (such as the methods described below).

The following procedures are exemplary of suitable protein purification procedures: by fractionation on an ion-exchange column; ethanol precipitation; reverse phase HPLC; chromatography on silica, chromatography on heparin SEPHAROSE™ chromatography on an anion or cation exchange resin (such as a polyaspartic acid column, DEAE, etc.); chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of polypeptides of the present application. Various methods of protein purification may be employed and such methods are known in the art and described for example in Deutscher M. P., Maintaining protein stability, Methods in Enzymology, 1990; 182:83-89; Scopes, Protein Purification: Principles and Practice, Springer-Verlag, New York, 1982. The purification step(s) selected will depend, for example, on the nature of the production process used and the particular polypeptide of the present application produced.

Tissue Scaffold

In another aspect, the present disclosure provides three-dimensional tissue scaffolds comprising a stem cell attracting element provided herein (e.g. a fusion protein comprising SDF-1α linked to CBD) releasably bound to a matrix.

The term "tissue scaffold" as used herein refers to a biocompatible three dimensional support structure which can be implanted at or otherwise placed in proximity with a living tissue. The tissue scaffold can carry one or more bioactive agents whose release from the scaffold can enhance repair and/or regeneration of the living tissue. In certain embodiments, the tissue scaffold may also provide for controlled release of the bioactive agent with respect to the release amount, timing and/or duration.

The tissue scaffold is biocompatible, which means it is compatible with living tissue or a living system, i.e. not toxic, not causing significant adverse effects such as sensitization, irritation to surrounding tissues, and does not cause any significant immunological rejection.

The tissue scaffold provided herein is three-dimensional, which means the scaffold has a spatial structure and is not in a linear structure. The tissue scaffold can be in any suitable form or shape, such as, for example, a patch, a block, a foam, a sponge, a granule, implant coatings, and other suitable three-dimensional shapes or forms. The various shapes or forms may be obtained by extrusion, injection molding, solvent casting, leaching methods, compression molding and rapid prototyping (including 3D Printing, Multi-phase Jet Solidification, and Fused Deposition Modeling (FDM)), and other suitable methods.

The tissue scaffold comprises a stem cell attracting element provided herein releasably bound to a matrix. The matrix as used herein comprises a biocompatible polymer. The term "polymer" as used herein is intended to encompass both biopolymers (such as protein, polypeptides, and polynucleotides), and synthetic polymers. Examples of biopolymers include collagen, keratin, silk, polysaccharide, dextran and its derivative, agarose, cellulose and its derivative, chitosan, hyaluronic acid, and derivatives. Examples of biocompatible synthetic polymers include, polylactic acid (PLA), polyglycolic acid (PGA), polylactic-co-glycolic acid (PLGA), polycaprolactone, poly-3-hydroxybutyrate, poly (p-dioxanone) and copolymers thereof, polyhydroxyalkanoate, poly(propylene fumarate), poly(ortho esters), and polyanhydrides. The polymer matrix can be made into a three-dimensional scaffold compatible for tissue implantation, and the stem cell attracting element can be loaded to the polymer matrix scaffold.

In certain embodiments, the matrix is biodegradable. "Biodegradable" as used herein means that the matrix is capable of being completely or substantially degraded, eroded or absorbed when exposed to either an in vivo environment or an in vitro environment having physical, chemical, or biological characteristics substantially similar to those of the in vivo environment within a living organism. In certain embodiments, the matrix can be absorbed or degraded gradually so that finally the tissue where the matrix is implanted at or adjacent to becomes indistinguishable from the surrounding tissue.

In certain embodiments, the matrix comprises collagen. In certain embodiments, the matrix comprises a polymer matrix (e.g. synthetic polymer) and collagen conjugated onto the polymer matrix. The conjugation can be covalent, for example, through a bifunctional linker such as N-hydroxysuccinimide (NHS) or 3-(2-pyridyldithio)propionyl hydrazide (PDPH); or can be non-covalent, for example, through biotin-strepavidin bonding.

Collagen can be synthetic or naturally derived. Natural sources of collagen may be obtained from animal or human sources. For instance, it may be derived from tendons, bones, cartilages, ligaments, muscle, fascia, skin, cartilage, tail, or any source of collagenous tissue, in species such as rat, pig, cow, or human tissue or tissue from any other species. In certain embodiments, the collagen is type I, type II, type III or type IV collagen. In certain embodiments, the collagen is type I collagen. Synthetic collagen is collagen material which has been formed, and/or chemically/physically created or changed from its naturally-occurring state, for instance, the constituent amino acid(s) may be modified with other functional groups, such as acylated collagens and esterified collagens.

In certain embodiments, the matrix is a three-dimensional collagen scaffold which is made of collagen. Three-dimensional collagen scaffold can be fabricated using suitable methods, for example, without limitation, freeze-drying, emulsifying, gas foaming, supercritical fluid technology, sol-gel technique, melt molding technique, powder compaction, phase separation, electro-spinning, fiber bonding, fiber mesh, rapid prototyping, leaching, or the combination thereof, emulsion templating, as described by Garg, T. et al., Scaffold: a novel carrier for cell and drug delivery, Critical reviews in therapeutic drug carrier systems, 2012; 29 (1): 1-63, the content of which is incorporated herein by reference in its entirety.

In certain embodiments, the three-dimensional collagen scaffold is porous. The pores of the collagen scaffold can be observed under a microscope, such an electron microscope. In certain embodiments, the three-dimensional collagen scaffold has at least 50% to 90% of porosity, or about 60% to 85% of porosity, or about 70% to 85% of porosity, or about 75% to 85% of porosity, or about 75% to 80% of porosity, or about 80% to 85% of porosity. In certain embodiments, the three-dimensional collagen scaffold has at least about 50% of porosity, at least about 55% of porosity, at least about 60% of porosity, at least about 65% of porosity, at least about 70% of porosity, at least about 75% of porosity, or at least about 80% of porosity. The porosity can be determined using any suitable methods. For example, the porosity can be calculated from inherent density of the collagen material and apparent density of the scaffold, using the equation:

$$\text{porosity} = \left(1 - \frac{\text{apparant density}}{\text{inherent density}}\right) \times 100\%.$$

Alternatively, the porosity can also be calculated based on void fraction, $$\text{i.e.} \frac{\text{void} - \text{space volume}}{\text{bulk volume}},$$

where bulk volume is the total volume of the three-dimensional collagen scaffold, and the void-space volume is the empty space or pore volume.

The three-dimensional collagen scaffold can have a majority of pores (e.g. at least 80%, 70%, 60%, 50%) having a pore size ranging from about 10-100 μm (for example, about 10-80 μm, about 15-80 μm, about 20-70 μm, about 20-60 μm, about 20-50 μm, about 20-40 μm, about 20-35 μm, or about 20-30 μm). "Pore size" as used herein means the longest dimension of the pore. Determination of pore size can be performed under electron scanning microscope, based on the scale and the SEM image.

In certain embodiments, the three-dimensional collagen scaffold is in membrane form (i.e. membrane scaffold). The membrane scaffold can have a thickness of about 0.5-3 mm (for example, 0.5-2.5 mm, 0.5-2 mm, 0.5-1.5 mm, 0.5-1 mm, or about 1 mm).

The overall size and shape of the three-dimensional collagen scaffold can be made to suit the intended application. For example, if the collagen scaffold is intended to be implanted in vivo to promote tissue repair, then the size and shape can be made to suit the tissue to be repaired.

The stem cell attracting element can be releasably bound to the matrix in any means that can immobilize the stem cell attracting element onto the matrix and also allow release of the stem cell attracting element under physiological conditions. In certain embodiments, the stem cell attracting element is bound to the matrix through non-covalent bond such as hydrogen bonds, hydrophobic interactions, Van der Waals forces, ionic bonds, magnetic force, or avidin-, streptavidin-, and Neutravidin-biotin bonding. The stem cell attracting element can be bound to the matrix during the formation of the matrix or after the matrix has been formed.

In certain embodiments, the stem cell attracting element is releasably bound to the three-dimensional collagen scaffold through the binding of the CBD domain of the stem cell attracting element to the collagen scaffold. The stem cell attracting element can be bound to the three-dimensional collagen scaffold by any suitable methods. For example, three-dimensional collagen scaffold can be soaked in a solution of the stem cell attracting element and incubated for a period of time sufficient to allow binding of the stem cell attracting element to the collagen scaffold. After incubation, the tissue scaffold can be taken out of the solution, and allowed to be dried for further use.

In certain embodiments, the stem cell attracting element on the tissue scaffold can be released in a sustained manner wherein the stem cell attracting element is gradually and steadily released from the scaffold over a time period suitable to enhance tissue repair and/or regeneration.

In certain embodiment, no more than 20% (e.g. about 20%) of the stem cell attracting element is released from the tissue scaffold (e.g. the 3D collagen scaffold) over a time period of at least 3 days (e.g. 3, 4, 5, or 6 days), no more than 30% (e.g. about 30%) of the stem cell attracting element is released from the tissue scaffold (e.g. the 3D collagen scaffold) over a time period of at least 5 days (e.g. 5, 6, 7, or 8 days), no more than 40% (e.g. about 40%) of the stem cell attracting element is released from the tissue scaffold (e.g. the 3D collagen scaffold) over a time period of at least 7 days (e.g. 7, 8, 9 or 10 days), or no more than 50% (e.g. about 50%) of the stem cell attracting element is released from the tissue scaffold (e.g. the 3D collagen scaffold) over a time period of at least 9 days (e.g. 9, 10, 11, or 12 days). The release of the stem cell attracting element from the tissue scaffold can be determined in vitro under conditions that simulate in vivo physiological conditions, for example, at a temperature of 37° C. and in the presence of a flow.

In certain embodiments, the tissue scaffold comprises a suitable amount of pre-loaded stem cell attracting element, depending on the intended use. "Pre-load" as used herein means the stem cell attracting element has been loaded to the matrix in a releasably binding manner before use of the matrix for attracting stem cells. In certain embodiments, the tissue scaffold comprises 1-10 mg, 1 μg-1000 μg, 1 μg-500 μg, 1 μg-300 μg, 1 μg-200 μg, 1 μg-100 μg, 10 μg-100 μg, 20 μg-100 μg, 30 μg-100 μg, 40 μg-100 μg, 50 μg-100 μg, 60 μg-100 μg, 70 μg-100 μg, 80 μg-100 μg, 90 μg-100 μg, 10 μg-90 μg, 10 μg-80 μg, 10 μg-70 μg, 10 μg-60 μg, 10 μg-50 μg, or 20 μg-50 μg of pre-loaded stem cell attracting element. In certain embodiments, the tissue scaffold comprises 10 μg-100 μg of the pre-loaded stem cell attracting element. The desired amount of loaded stem cell attracting element can be determined based on the release profile, time of action, and intended dose amount.

The three-dimensional collagen scaffold provided herein has many advantages. Because the collagen scaffold non-covalently binds to the CBD-SDF-1α, it can provide controlled and sustained release of CBD-SDF-1α, by continuously disassociating CBD-SDF-1α from the collagen scaffold under physiological conditions. Sustained release of CBD-SDF-1α allows for continuous recruitment of stem cells to the target site, and therefore ensures that a sufficient number of stem cells are recruited to the target site. For the recruited stem cells to perform the intended function such as tissue repair, they must be functional or at least survive at the target site. The three-dimensional collagen scaffold provided herein can provide a suitable microenvironment for stem cell infiltration, adhesion and differentiation, and therefore promote a niche environment that favors long-term survival and differentiation of the stem cells, which can contribute to promotion of angiogenesis, replenishment of dysfunctional cells and improvement of tissue function. Without a favorable microenvironment, the recruited stem cells would be difficult to survive at the local environment and usually have a poor long-term survival rate. The recruited stem cells can secrete growth factors and cytokines that can reduce scar formation and promote regeneration of injured tissue, for example, chronically injured tissue which could otherwise be covered by scars. Furthermore, the three-dimensional collagen scaffold not only provides a support for tissue growth and repair, it can also provides good mechanical properties to effectively withstand forces of body fluid flow or repeated cardiac contractions when used for cardiac repair.

Methods of Use

In another aspect, the present disclosure also provides methods of treating a subject by using the stem cell attracting element provided herein or the tissue scaffold provided herein.

The term "treat" as used herein is intended to encompass meanings including (i) preventing or alleviating an injury, disease, pathologic or medical condition; (ii) preventing or delaying the development or worsening of an injury, disease, pathologic or medical condition; (iii) promoting the healing of the injury, disease, pathologic or medical condition; (iv) reducing or ending symptoms associated with the injury, disease, pathologic or medical condition; and/or (v) restoring biological function of the injured tissue.

The subject can be an animal, or more preferably a mammal such as human, primate, rodent, canine, feline, bovine, ovine, equine, swine, caprine, and the like.

In certain embodiments, the present disclosure provides methods of mobilizing stem cells to a target tissue in a subject, comprising administering an effective amount of the stem cell attracting element (e.g. fusion protein comprising a stem cell attracting factor linked to CBD) provided herein to the target tissue. The stem cell attracting element can be administered using any suitable methods, such as, local injection, implantation or other suitable methods.

In certain embodiments, the stem cells express CXCR4. In certain embodiments, the stem cells can include, for example, progenitor cells, hematopoietic stem cells, and somatic stem cells. In certain embodiments, the stem cells are endogenous stem cells from the systemic circulation or the surrounding heart tissues of the subject undergoing treatment. In certain embodiments, the stem cells are exogenous stem cells that are cultured in vitro or extracted from a different subject.

Effective amount of the stem cell attracting element would generally depend on various factors known in the art, such as, for example, the age and condition of the subject, route of administration, release profile of the fusion protein, the nature of the condition being treated, and potential for adverse side-effects, and may be proportionally reduced or increased by one of ordinary skill in the art (e.g., physician or veterinarian) as indicated by these and other circumstances or requirements. In vitro activity and in vivo activity in animal models can also be used to aid the determination of effective amount in human subjects, using methods known in the art to extrapolate effective amounts in experimental animals to human.

In certain embodiments, the present disclosure provides methods of mobilizing stem cells to a target tissue in a subject, comprising introducing the tissue scaffold provided herein to the target tissue.

In certain embodiments, the tissue scaffold is introduced to be in contact with the target tissue. The term "in contact" as used herein means in touch or in immediate or close proximity, so as to bring about intended physiological effects. The tissue scaffold described herein can be introduced into a body by surgical or non-surgical methods. For example, the tissue scaffold can be implanted adjacent to the target tissue (e.g. cardiac tissue), optionally sutured or otherwise fixed on the target tissue.

Examples of target tissue include, for example, a cardiac tissue, brain tissue, spinal cord tissue, muscle tissue or skin tissue. In certain embodiments, the target tissue is an injured tissue. The injury may be due to tissue damage caused by pathological condition (for example tissue damage caused by lack of sufficient oxygen or blood supply), or external damage such as trauma and burn.

In certain embodiments, the present disclosure provides methods of promoting repair of an injured tissue in a subject in need thereof, comprising introducing the tissue scaffold provided herein to the injured tissue. In certain embodiments, the injured tissue is injured cardiac tissue, injured brain tissue, injured spinal cord tissue, injured muscle tissue or injured skin tissue.

In certain embodiments, the present disclosure provides methods of treating myocardial infarction in a subject in need thereof, comprising introducing the three-dimensional collagen scaffold provided herein to a cardiac tissue affected by the myocardial infarction.

Myocardial infarction is characterized in lack of blood flow to part of the heart, leading to loss of myocadiocytes, scar formation, and ventricular remodeling in the affected part. By introducing the three-dimensional collagen scaffold to the affected cardiac tissue, the stem cell attracting element (e.g. fusion protein of CBD-SDF-1α) can be locally released in a sustained manner, therefore induce homing of endogenous or exogenous stem cells from systemic circulation or the stem cells surrounding heart to the affected tissue, where dysfunctional myocadiocytes are replenished, new blood vessels and microvessel are formed, and eventually lead to repair and/or regeneration of the infarcted cardiac tissue, and also increase in capillary density and improvement in cardiac function.

In addition to the stem cell mobilization, the three-dimensional collagen scaffold has good mechanical properties to withstand forces of repeated cardiac contractions, and therefore can restrain left ventricle and prevent chamber dilation by providing mechanical support to compensate for intraventricular pressure. All publications and patents cited in this specification are herein incorporated by reference to their entirety.

EXAMPLES

The invention will be more readily understood with reference to the following examples, which are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Statistical Analysis

Statistics were performed with SPSS software for Windows (version 13.0, SPSS Inc, Chicago, Ill.). Comparisons among multiple groups were performed by one-way analyses of variance (ANOVA) followed by the Bonferroni-Dunn test. Comparisons between two groups were performed using the unpaired Student's t-test. All data are expressed as mean±SEM, the value of P<0.05 was considered to be significantly different.

Example 1: Cloning, Expression and Purification of SDF-1α

Figure 1:
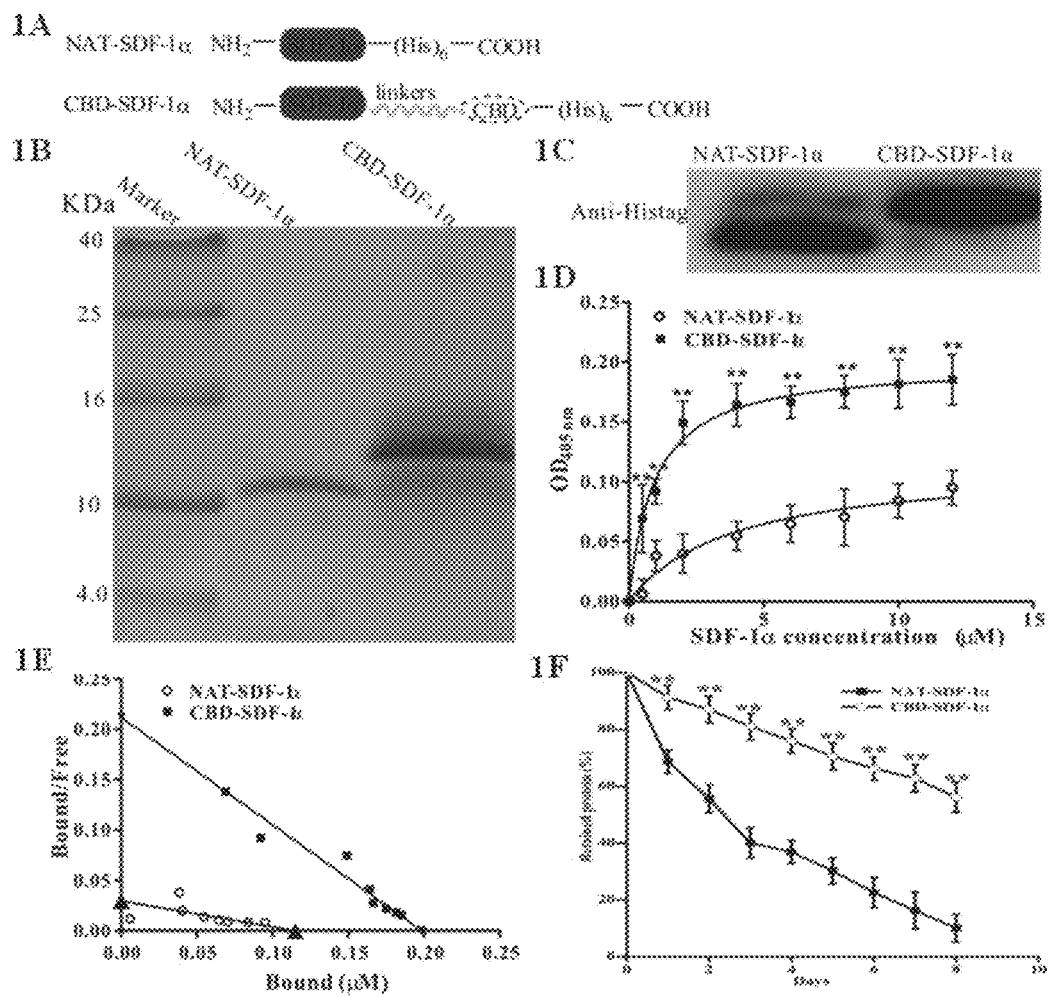
FIG. 1 shows in vitro characterization results of native (NAT)-SDF-1α and collagen binding domain (CBD)-SDF-1α. Data are presented as means±SEM, **P<0.01.

Native human SDF-1α (NAT-SDF-1α) gene was amplified from cDNA of human fibroblasts by polymerase chain reaction. CBD-SDF-1α was constructed by incorporating the collagen-binding domain (CBD) to the C-terminal of NAT-SDF-1α. To avoid affecting the bioactivity of SDF-1α, the collagen-binding domain was fused to the C-terminal of NAT-SDF-1α and they were spaced by a linker (FIG. 1A). The NAT-SDF-1α and CBD-SDF-1α sequence were inserted into a pET28a vector (Novagen, Madison, Wis.), and then transformed into a BL21 strain (DE3) of *Escherichia coli* (Novagen) for protein expression, respectively. Both proteins containing 6×His were purified using a nickel chelate chromatography column (GE Healthcare, Chalfont St Giles, United Kingdom), and identified by Tricine SDS-PAGE (FIG. 1B) and Western blot (FIG. 1C) using antipolyhistidine monoclonal antibody (1:3000; Sigma-Aldrich, St. Louis, Mo.).

Example 2: Collagen-Binding and Release Experiments In Vitro

To measure the collagen-binding ability of CBD-SDF-1α in vitro, a modified ELISA was performed. Type I collagen solution prepared from rat tail tendon (de Souza S J and Brentani R., Collagen Binding Site in Collagenase Can Be Determined Using the concept of sense-antisense peptide interactions, J Biol Chem. 1992; 267:13763-13767) was added into a 96-well plate. The plate was left at 4° C. overnight and then ventilated dry after discarding redundant solution. After washing and blocking, NAT-SDF-1α or CBD-SDF-1α solution at increasing concentrations were added to the plate (100 µL/well) and incubated at 37° C. for 2 h, and then washed 3 times to remove unbound proteins. Retained proteins on collagen were detected by a primary antibody against polyhistidine and an alkaline phosphatase-conjugated secondary antibody (1:10,000; Sigma-Aldrich). Optical Density (OD) values were quantified at 405 nm using an ELISA reader (FIG. 1D) and dissociation constant (Kd) values of NAT-SDF-1α and CBD-SDF-1α from collagen were calculated by Scatchard analysis using GraphPad Prism with the measured OD values (FIG. 1E).

As shown in FIG. 1D, OD values of CBD-SDF-1α were significantly higher than that of NAT-SDF-1α (n=6, P<0.01) at the same concentration, suggesting that more CBD-SDF-1α bound to type I collagen than NAT-SDF-1α did (FIG. 1D). The dissociation constant (Kd) values of NAT-SDF-1α and CBD-SDF-1α from collagen were calculated by Scatchard analysis and the slope of the resulting straight line equaled −1/Kd. As shown in the Scatchard plot of FIG. 1E, Kd values of NAT-SDF-1α or CBD-SDF-1α were respectively 1.339 and 0.254 µM, and the lower Kd of CBD-SDF-1α represented a greater affinity to collagen.

In the releasing assay, chemokine (i.e. NAT-SDF-1α or CBD-SDF-1α) bound to the collagen-coated 96-well plate was treated in advance as depicted above and 200 µL PBS was added into each well. The plate was incubated on a rocker platform (37° C., 80 g) to simulate body fluid, and the samples were collected and replaced with PBS every 24 h. At each time point from day 0 to 8, the concentration of SDF-1α in the samples was analyzed with a human SDF-1α ELISA kit according to the manufacturer's protocol (Bluegene, Shanghai, China).

As shown in FIG. 1F, a large amount of NAT-SDF-1α was quickly released on the first day, whereas CBD-SDF-1α gradually released from collagen. At day 8, 56.1% of CBD-SDF-1α retained on collagen, but 10.1% of NAT-SDF-1α was retained (P<0.01). Data showed that CBD-SDF-1α could be released controllably from collagen.

Example 3: Chemotactic Activity Test of NAT-SDF-1α and CBD-SDF-1α

A modified Boyden chamber (8 µm, Corning Costar Corp., Cambridge, Mass.) assay was performed to test chemotactivity of NAT-SDF-1α or CBD-SDF-1α. Briefly, 600 µL NAT-SDF-1α (100 ng/mL), 600 µL CBD-SDF-1α (100 ng/mL) or medium alone (control) was added into the lower chamber and 200 µL mouse hemapoietic stem cell (mHSCs) or human mesenchymal stem cell (hMSCs) were seeded into the upper chamber at a density of $2 \times 10^4$ cells/mL. After incubation at 37° C. for 4 h, samples were fixed and stained with crystal violet. Mean numbers of migrated cells were observed and counted by a microscopy from five fields (200×). The migration index was calculated to express stimulated migration using the following equation: Migration index=Stimulated migration/Random migration. Data showed that both NAT-SDF-1α and CBD-SDF-1α could significantly mediate hHSC (FIG. 2A) and mMSC (FIG. 2B) migration compared with the control group (medium alone) (n=6, p<0.01 for both proteins), respectively, at 100 ng/mL, and there was no significant difference between NAT-SDF-1α and CBD-SDF-1α (FIG. 2A, 2B), which demonstrated that bioactivity of SDF-1α was not affected by fusion with CBD peptides at the C-terminal.

Example 4: Chemotactic Activity Test of Collagen Gels Modified with NAT-SDF-1α and CBD-SDF-1α

To analyze whether CBD-SDF-1α could enrich more stem cells via a ligand-receptor interaction, mHSCs and hMSCs were prepared and incubated with collagen gel modified with NAT-SDF-1α or CBD-SDF-1α, respectively. Mouse c-kit positive (c-kit⁺) hematopoietic stem cells (mHSCs) were freshly isolated from the bone marrow of 4-week-old male C57BL/6J mice with a magnetic activated cell sorting kit (BD Bioscience, Heidelberg, Germany) and human placenta-derived mesenchymal stem cells (hMSCs) were isolated from neonatal placentas of healthy volunteer as described previously (Wang Y et al., Effects of hypoxia on osteogenic differentiation of rat bone marrow mesenchymal stem cells, Molecular and cellular biochemistry. 2012; 362:

25-33). The adhesion assay was performed to detect the adhesive ability of mHSC and hMSC. Briefly, chemokine-modified collagen gel was prepared as the binding assay in a 24-well plate. mHSCs and hMSCs were seeded into each well ($2 \times 10^4$/well), respectively, and medium was discarded after incubation at 37° C. for 1 h. Gently washed with PBS, retained cells were fixed with 4% paraformaldehyde and stained with Hoechst 33342 for 15 min. Six fields-of-view were imaged randomly using a Zeiss Z1 fluorescent microscope and Hoechst-positive cells were counted.

Values were standardized with the control group. The results showed that, CBD-SDF-1α loaded on a collagen membrane increased the adhesion of hMSCs by 7.07-fold (FIG. 2C, 2E), or increased the adhesion of mHSCs by 13.29-fold (FIG. 2D, 2F) compared with a blank collagen scaffold (control) (p<0.01), whereas NAT-SDF-1α loaded on a collagen membrane could not effectively enrich HSCs or MSCs because SDF does not retain in the collagen membrane.

Example 5: CBD-SDF-1α-binding Ability in Rat Infarcted Hearts

Male Sprague-Dawley (SD) rats (180-200 g) were used for the acute myocardial infarction (AMI) model. Briefly, rats were anesthetized with sodium pentobarbital (40 mg/kg). After a thoracotomy was performed at the left fourth intercostal space, the left anterior descending coronary artery (LAD) was permanently ligated with a 6-0 silk suture below the tip of the left atrial appendage. Immediately after the left anterior descending coronary artery ligation, 1.0 nmol NAT-SDF-1α or CBD-SDF-1α dissolved in 100 μL PBS was injected into the infarcted border zone at 5 sites. In control group, 100 μL PBS was injected into the similar zone. After injection, routine chest closure was performed and rats were allowed to recover on a heating pad.

To detect retained SDF-1α at the ischemic border, rat hearts were harvested at 3 h or 6 h after injection. Peri-infarct zones were removed and frozen immediately in liquid nitrogen for protein extraction. Western blot with the primary antibody against polyhistidine was used to distinguish exogenous SDF-1α from endogenous proteins. Meanwhile, SDF-1α in serum was measured via a human SDF-1α ELISA kit (Bluegene, Shanghai, China) at each time point.

As shown in FIGS. 3A and 3B, NAT-SDF-1α bound to the ischemic area was detected at 3 h but mostly decreased at 6 h after injection. In contrast, CBD-SDF-1α diminished slowly and substantial CBD-SDF-1α was detected in the ischemic area at 6 h. To confirm that decreased NAT-SDF-1α or CBD-SDF-1α diffused into the peripheral blood, we measured serum SDF-1α at 3 h and 6 h after injection. As shown in FIG. 3C, SDF-1α in the NAT-SDF-1α group exceeded that of the CBD-SDF-1α group. Thus, NAT-SDF-1α diffused quickly in vivo, but CBD-SDF-1α could bind to endogenous collagen, and thereby maintain a high concentration and achieve controlled release.

Example 6: CBD-SDF-1α Increases c-kit+ Stem Cell Homing to the Infarcted Heart

To demonstrate whether controlled release of CBD-SDF-1α enhanced recruitment of endogenous stem cells, we used c-kit as a marker to detect stem cell 4 days after AMI model was made according to Example 5.

As shown in FIGS. 3D and 3E, local delivery of CBD-SDF-1α recruited more c-kit+ stem cell homing to the infarcted heart than control (an injection of 100 μL PBS only) and NAT-SDF-1α groups (P<0.01, respectively), and the recruited stem cells may be important for cardiac regeneration and repair.

Example 7: Analysis of Cardiac Function by Echocardiography after CBD-SDF-1α Injection Twelve weeks after the AMI model was made according to Example 5, cardiac function was evaluated by echocardiography. Echocardiography was performed using a 10-MHz linear transducer and a cardiovascular ultrasound system (SONOS model 5500, Hewlett-Packard, Palo Alto, Calif.) to assess cardiac function. Left ventricular (LV) end-systolic dimension (LVDs) and end-diastolic dimension (LVDd) were measured in M-mode tracings at the midpapillary level. To examine systolic function, the LV end-diastolic volume (LVEDV), LV end-systolic volume (LVESV), ejection fraction (EF), and fractional shortening (FS) were measured.

As shown in Table 1, LV fractional shortening and ejection fractions were significantly higher in the CBD-SDF-1α group than that in NAT-SDF-1α and control groups (P<0.01, respectively). No significant difference was found in LVDd, LVDs, IVSDT, or LVPWT among the control, NAT-SDF-1α, and CBD-SDF-1α groups.

TABLE 1

Evaluation of Cardiac Function by Echocardiography (12 Weeks after Injection)

| Groups | LVDd, cm | LVDs, cm | IVSDT, cm | LVPWT, cm | EF, % | FS, % |
| --- | --- | --- | --- | --- | --- | --- |
| Control | 0.73 ± 0.026 | 0.45 ± 0.106 | 0.13 ± 0.034 | 0.22 ± 0.005 | 42.54 ± 2.1 | 18.35 ± 1.4 |
| NAT-SDF-1α | 0.71 ± 0.013 | 0.51 ± 0.037 | 0.15 ± 0.016 | 0.23 ± 0.007 | 57.69 ± 1.8 | 26.85 ± 2.3 |
| CBD-SDF-1α | 0.69 ± 0.041 | 0.40 ± 0.029 | 0.14 ± 0.028 | 0.25 ± 0.019 | 72.14 ± 1.6* | 36.36 ± 1.5* |

FS indicates fractional shortening;

EF, ejection fraction;

LVDd, left ventricular end-diastolic dimension;

LVDs, left ventricular end-systolic dimension;

IVSDT, interventricular septal diastolic thickness; and

LVPWT, left ventricular posterior wall thickness.

Data are mean ± SD, n = 8 in each group.

*P < 0.01 vs control.

Example 8: Histological Analysis of Scar Size, LV Wall Thickness after MI with CBD-SDF-1α Injection All hearts were harvested after echocardiographic measurement and fixed in 4% paraformaldehyde. Samples were embedded in paraffin, cut (4-μm sections), and mounted on positively charged glass slides. Masson trichrome-staining was prepared for analysis of scar size and left ventricle (LV) wall thickness. Anti-α-sarcomeric actin (α-SMA) antibody (1:200; Abcam) was used to evaluate positive cardiomyocytes and anti-Von Willebrand Factor (vWF) antibody (1:500; Abcam) was used to evaluate the density of capillary vessels. Image-Pro Plus software was used for quantification as follows: the number of capillary vessels was counted and the percentage of α-SMA positive area=α-SMA positive area/total area.

As shown in FIG. 4, scar size in the CBD-SDF-1α group (18.7±4.62%) was significantly reduced compared with the control (48.39±5.68%) and NAT-SDF-1α (31.83±6.75%) groups (P<0.01, respectively). The protective effects were also reflected by the infarcted wall thickness. The wall thickness in the CBD-SDF-1α group (2.73±0.39 mm) was significantly greater than that in the NAT-SDF-1α (1.52±0.39 mm) and control (1.25±0.41 mm) groups (PBS only) (P<0.01, respectively).

Although our data show that CBD-SDF-1α can improve cardiac function and reduce scar size, the myocardium ultimately requires vascularization for cardiomyocyte long-term survival. Hence, we measured the density of the capillary vessels at 12 weeks after myocardial infarction (MI) using an antibody to Von Willebrand Factor, a marker of the mature microvasculature. As shown in FIG. 5A, the capillary vessels (shown as brown dots in the image) were scarce at the border zone in the control group, modest in the NAT-SDF-1α group, but were in a significantly higher density in the CBD-SDF-1α-treated group. FIG. 5B showed quantified results of FIG. 5A, which showed significantly greater capillary density at the border zone in CBD-SDF-1α-treated hearts (275.61±18.25/mm$^2$) compared with that of NAT-SDF-1α (183.28±20.36/mm$^2$) and control (161.49±17.92/mm$^2$) groups (PBS only) (FIG. 5B). This clearly demonstrated that controlled release of CBD-SDF-1α was important for angiogenesis, and that CBD-SDF-1α promotes angiogenesis after MI.

Example 9: Construction of Cardiac Patches and Sustained Release Experiments In Vitro 3D collagen membrane scaffolds were prepared with good biodegradability and biocompatibility (FIG. 6), to provide a favorable microenvironment for stem cell infiltration, adhesion, and differentiation.

To prepare the 3D collagen membrane scaffold, bovine skin was peeled from the dermis portion and treated in a 1% SDS solution for 48 hours followed by treatment with a 1% Triton solution (Sigma, dissolved in water) for 24 hours. The skin was then treated with 25-100 mmol/L Tris-HCl buffer (pH 7.6) containing 0.5-1.5 mol/L NaCl for 24 hours. The product was rinsed with deionized water and freeze-dried, to yield the 3D collagen membrane.

Scanning electron microscope (SEM) analysis was performed with the 3D collagen membrane as prepared, and pore size was determined by measuring the dimension of each pore with the scale, calculating the pore size and its distribution. An exemplary SEM image of the 3D collagen membrane is shown in FIG. 6F. The majority of the pores had a pore size ranging from 20 to 30 μm. The porosity of the 3D collagen membrane was also determined by the formula (1−the apparent density/inherent density)*100%, where the apparent density was calculated by dividing the mass of the collagen membrane by the gross volume of the collagen membrane, and the inherent density is the density of the collagen material per se. The porosity of the collagen membrane was determined to be about 80%.

Collagen membranes (having a thickness of 1 mm and a cross-section length of about 1 cm) were cut into 6×6 mm pieces in advance, and 1.0 nmol NAT-SDF-1α or CBD-SDF-1α was added onto them, respectively. After incubation at 37° C. for 2 h, collagen membranes as cardiac patches were dried. The in vitro release experiments for 3D collagen membrane scaffolds were carried out. Briefly, 3D collagen membrane with 1.0 nmol NAT-SDF-1α or CBD-SDF-1α was incubated with PBS in a plate. The plate was on a rocker platform (37° C., 80 g) to simulate body fluid, and the samples were collected and replaced with PBS every 24 h. At each time point from day 0 to 9, the concentration of NAT-SDF-1α or CBD-SDF-1α in the samples was analyzed with a human SDF-1α ELISA kit according to the manufacturer's protocol (Bluegene, Shanghai, China).

The release was measured from day 0 to day 9. As shown in FIG. 9, NAT-SDF-1α was quickly released from day 3, whereas CBD-SDF-1α gradually released from the 3D collagen membrane scaffolds. At day 9, about 50% of CBD-SDF-1α retained on the collagen scaffold, but only about 10% of NAT-SDF-1α was retained (P<0.05). Data showed that collagen membrane along with CBD-SDF-1α offered improvements, and CBD-SDF-1α release was controlled from the collagen membrane for the recruitment of endogenous stem cells.

Example 10: Measurement of Stem Cells Recruitment In Vivo

Similar to Example 9, collagen membranes (having a thickness of 1 mm and a cross-section length of about 1 cm) were cut into 6×6 mm pieces in advance, and 1.0 nmol NAT-SDF-1α or CBD-SDF-1α was added onto them, respectively, and incubated at 37° C. for 2 h. For control group, the collagen membranes were incubated with PBS only. The collagen membranes were implanted into the rat cardiac defect model. Briefly, after the heart was exposed, a transmural defect with 5×5 mm in size was created on the left ventricular wall and the prepared patch was immediately sutured on the myocardium with a 6-0 silk suture to cover the defective part.

Immunofluorescent staining was used to identify endogenous stem cell homing to the ischemic area or cardiac patches. Hearts were harvested 4 days after surgery and embedded in optimal cutting temperature (O.C.T) compound (Tissue-Tek, Sakura, Japan). Frozen sections (5-μm thickness) were prepared and incubated with antibodies against stem cell biomarkers, i.e. primary antibody against c-kit (1:200; Abcam, Cambridge, Mass.) or Flk (1:100; Abcam), at 4° C. overnight. After washing, sections were incubated with FITC-conjugated Donkey anti-mouse IgG (1:500; Abcam) or PE-conjugated goat anti-rabbit IgG (1:500; Abcam) at room temperature for 2 h and nuclei were counterstained with DAPI. Six fields of each sample were imaged randomly by confocal microscopy and measured by an observer blind to treatment group with an Image-pro Plus software (Media Cybernetics, Version 6.0).

At 4 days after implantation, immunofluorescent staining results confirmed that CBD-SDF-1α modified collagen membranes recruited more c-kit+ stem cells and Flk+ cells (FIG. 7) compared with NAT-SDF-1α and control groups (n=6, P<0.01). Also, no inflammatory or adhesive reactions were identified, suggesting that collagen membranes are biocompatible. Recruited stem cells may contribute to promotion of angiogenesis, replenishment of dysfunctional cells and improved cardiac function. Results also showed that 3D collagen membrane scaffolds were advantageous. Because infarcted area was replaced with old scar tissue, stem cells cannot easily infiltrate and survive in this hostile microenvironment. The 3D collagen membrane scaffolds provided better support for stem cell adhesion and growth, thereby provided favorable microenvironment for the recruited stem cells.

Example 11: CBD-SDF-1α Modified Collagen Membrane Improves Cardiac Function

To measure the cardiac function of the rat cardiac defect model implanted with the collagen membrane, all rats that were manipulated according to Example 10 and were measured by echocardiography 12 weeks after surgery, and results showed that CBD-SDF-1α significantly increased LV fractional shortening and ejection fractions compared with control and NAT-SDF-1α groups. In contrast, NAT-SDF-1α also slightly increased ejection fractions but this was not significantly different from the control group and the fractional shortening was barely increased (Table 2).

TABLE 2

Evaluation of Cardiac Function by Echocardiography (12 Weeks after Implantation of Patches)

| Groups | LVDd, cm | LVDs, cm | IVSDT, cm | LVPWT, cm | EF, % | FS, % |
|---|---|---|---|---|---|---|
| Control | 0.68 ± 0.038 | 0.45 ± 0.026 | 0.20 ± 0.017 | 0.25 ± 0.006 | 68.60 ± 1.5 | 38.67 ± 1.9 |
| NAT-SDF-1α | 0.66 ± 0.025 | 0.41 ± 0.019 | 0.19 ± 0.020 | 0.27 ± 0.014 | 74.82 ± 1.7 | 38.77 ± 1.2 |
| CBD-SDF-1α | 0.67 ± 0.032 | 0.35 ± 0.029 | 0.23 ± 0.015 | 0.24 ± 0.026 | 83.73 ± 2.3* | 47.37 ± 2.2* |

FS indicates fractional shortening;
EF, ejection fraction;
LVDd, left ventricular end-diastol Example 12: CBD-SDF-1α Modified Collagen Membrane Promotes Angiogenesis and Myocardium Regeneration For rats in Example 11, hearts were harvested after echocardiographic measurement, and the collagen scaffolds were completely degraded, leaving only residual suture sites. Corresponding to the data from MI studies, histological images revealed that CBD-SDF-1α-modified patches had significantly greater capillary density (356.71±27.46/mm$^2$) compared with NAT-SDF-1α (237.06±31.69/mm$^2$) and control (193.86±19.52/mm$^2$) groups (FIG. 8A, 8C). Similarly, α-SMA-positive areas were larger in the CBD-SDF-1α group (38.1±2.64%) than that of NAT-SDF-1α (12.5±1.86%) and control groups (3.6±1.52%) (FIG. 8B, 8D). Therefore, a CBD-SDF-1α-modified collagen membrane promoted cardiac regeneration and angiogenesis and improved cardiac function.

The invention claimed is:

1. A fusion protein comprising a collagen binding domain linked to stromal cell-derived factor 1α (SDF-1α), wherein the fusion protein consists of the aminoacid sequence of SEQ ID NO: 9, wherein the fusion protein retains no less than 80% of biological activity of a native SDF-1α in attracting stem cells.

2. A three dimensional collagen scaffold comprising a fusion protein that is releasably bound to a matrix, wherein the fusion protein consists of the amino acid sequence of SEQ ID NO:9, wherein the fusion protein retains no less than 80% of biological activity of a native SDF-1α in attracting stem cells.

3. The collagen scaffold of claim 2, wherein the three-dimensional collagen scaffold is in membrane form.

4. The collagen scaffold of claim 2, wherein no more than 50% of the fusion protein is released from the collagen scaffold over a time period of 9 days.

5. The collagen scaffold of claim 2, wherein the matrix comprises collagen.

6. The collagen scaffold of claim 2, wherein the three-dimensional collagen scaffold is porous.

7. The collagen scaffold of claim 6, wherein the three-dimensional collagen scaffold has 50% to 90% of porosity.

8. The collagen scaffold of claim 2, wherein the fusion protein can be released from the three-dimensional collagen scaffold in a sustained manner.

9. The collagen scaffold of claim 8, wherein the collagen scaffold comprises 1 µg-1000 µg of the fusion protein pre-loaded to the collagen scaffold.

* * * * *

SEQUENCE LISTING

<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Thr Lys Lys Thr Leu Arg Thr
1               5

<210> SEQ ID NO 2
<211> LENGTH: 11
<212> TYPE: PRT
<213> ORGANISM: Artificial Sequence
<220> FEATURE:

<223> OTHER INFORMATION: Synthetic

<400> SEQUENCE: 2

Gly Ser Ala Gly Ser Ala Ala Gly Ser Gly Gly
1               5                   10

<210> SEQ ID NO 3
<211> LENGTH: 68
<212> TYPE: PRT
<213> ORGANISM: Artificial Sequence
<220> FEATURE:
<223> OTHER INFORMATION: Synthetic

<400> SEQUENCE: 3

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 4
<211> LENGTH: 107
<212> TYPE: PRT
<213> ORGANISM: Artificial Sequence
<220> FEATURE:
<223> OTHER INFORMATION: Synthetic

<400> SEQUENCE: 4

Met Gly Ser Ser His His His His His His Ser Ser Gly Leu Val Pro
1               5                   10                  15

Arg Gly Ser His Met Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Gly Ser Ala Gly Ser Ala Ala
                85                  90                  95

Gly Ser Gly Gly Thr Lys Lys Thr Leu Arg Thr
            100                 105

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
actaagaaaa ccctgcgtac t                                         21

<210> SEQ ID NO 6
<211> LENGTH: 33
<212> TYPE: DNA

```
<213> ORGANISM: Artificial Sequence
<220> FEATURE:
<223> OTHER INFORMATION: Synthetic

<400> SEQUENCE: 6
ggtagcgcgg gcagtgctgc gggttctggc ggt                                    33

<210> SEQ ID NO 7
<211> LENGTH: 204
<212> TYPE: DNA
<213> ORGANISM: Artificial Sequence
<220> FEATURE:
<223> OTHER INFORMATION: Synthetic

<400> SEQUENCE: 7
aagcccgtca gcctgagcta cagatgccca tgccgattct tcgaaagcca tgttgccaga       60
gccaacgtca agcatctcaa aattctcaac actccaaact gtgccttca gattgtagcc       120 cggctgaaga acaacaacag acaagtgtgc attgacccga agctaaagtg gattcaggag      180
tacctggaga aagctttaaa caag                                             204

<210> SEQ ID NO 8
<211> LENGTH: 324
<212> TYPE: DNA
<213> ORGANISM: Artificial Sequence
<220> FEATURE:
<223> OTHER INFORMATION: Synthetic

<400> SEQUENCE: 8
atgggcagca gccatcatca tcatcatcac agcagcggcc tggtgccgcg cggcagccat       60
atgaagcccg tcagcctgag ctacagatgc ccatgccgat tcttcgaaag ccatgttgcc      120
agagccaacg tcaagcatct caaaattctc aacactccaa actgtgccct tcagattgta      180
gcccggctga agaacaacaa cagacaagtg tgcattgacc cgaagctaaa gtggattcag      240
gagtacctgg agaaagcttt aaacaagggt agcgcgggca gtgctgcggg ttctggcggt      300
actaagaaaa ccctgcgtac ttga                                             324

<210> SEQ ID NO 9
<211> LENGTH: 86
<212> TYPE: PRT
<213> ORGANISM: Artificial Sequence
<220> FEATURE:
<223> OTHER INFORMATION: Synthetic

<400> SEQUENCE: 9

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Gly Ser Ala Gly Ser Ala Ala Gly Ser Gly Gly Thr
65                  70                  75                  80

Lys Lys Thr Leu Arg Thr
                85

<210> SEQ ID NO 10
<211> LENGTH: 261
```

```
<212> TYPE: DNA
<213> ORGANISM: Artificial Sequence
<220> FEATURE:
<223> OTHER INFORMATION: Synthetic

<400> SEQUENCE: 10
aagcccgtca gcctgagcta cagatgccca tgccgattct tcgaaagcca tgttgccaga      60
gccaacgtca agcatctcaa aattctcaac actccaaact gtgcccttca gattgtagcc     120
cggctgaaga acaacaacag acaagtgtgc attgacccga agctaaagtg gattcaggag     180
tacctggaga aagctttaaa caagggtagc gcgggcagtg ctgcgggttc tggcggtact     240
aagaaaaccc tgcgtacttg a                                               261
```